(12) United States Patent
Johnson

(10) Patent No.: US 11,268,063 B2
(45) Date of Patent: Mar. 8, 2022

(54) METHOD AND APPARATUS FOR TREATING BIOGAS

(71) Applicant: Energy Tech Innovations, LLC, Mukwonago, WI (US)

(72) Inventor: Bryan R. Johnson, Mukwonago, WI (US)

(73) Assignee: Energy Tech Innovations, LLC, Mukwonago, WI (US)

( * ) Notice: Subject to any disclaimer, the term of this patent is extended or adjusted under 35 U.S.C. 154(b) by 43 days.

(21) Appl. No.: 16/725,426

(22) Filed: Dec. 23, 2019

(65) Prior Publication Data

US 2020/0131468 A1 Apr. 30, 2020

Related U.S. Application Data

(63) Continuation-in-part of application No. 15/248,510, filed on Aug. 26, 2016, now Pat. No. 10,518,209.
(Continued)

(51) Int. Cl.
*C12M 1/00* (2006.01)
*C12M 1/107* (2006.01)
(Continued)

(52) U.S. Cl.
CPC ......... *C12M 47/18* (2013.01); *B01D 53/1475* (2013.01); *B01D 53/185* (2013.01);
(Continued)

(58) Field of Classification Search
USPC .................................................. 96/344, 353
See application file for complete search history.

(56) References Cited

U.S. PATENT DOCUMENTS 1,460,490 A 7/1923 Johnston
3,555,783 A * 1/1971 Grimshaw ............ C02F 3/1289
 95/177
(Continued)

FOREIGN PATENT DOCUMENTS

CN 203777898 U 8/2014
EP 0180670 A1 * 5/1986 ......... B01D 53/1475
WO 2011/152770 12/2011

OTHER PUBLICATIONS

International Search Report and the Written Opinion of the ISR; Application No. PCT/US2016/048951 dated Nov. 15, 2016—(9) pages.
(Continued)

*Primary Examiner* — Christopher P Jones
*Assistant Examiner* — Phillip Y Shao
(74) *Attorney, Agent, or Firm* — Boyle Fredrickson, SC

(57) ABSTRACT

Multiple risers are provided to perform different steps in a biogas water wash process. The risers may include absorption risers, flashing risers, and stripping risers. In each riser, the inlets to provide fluids to the riser and outlets to remove fluids from the risers are provided at one end of the riser. Each riser may then be located substantially below grade such that the end with the inlets and outlets is accessible at or just above the ground level. The risers within each step of the water wash process may be connected in series, parallel, or a combination thereof. The risers may also be constructed of a polyethylene material to reduce cost and weight of the water wash system.

17 Claims, 16 Drawing Sheets

Related U.S. Application Data

(60) Provisional application No. 62/211,494, filed on Aug. 28, 2015.

(51) Int. Cl.
*B01D 53/18* (2006.01)
*B01D 53/14* (2006.01)

(52) U.S. Cl.
CPC ....... *C12M 21/04* (2013.01); *B01D 2252/103* (2013.01); *B01D 2257/504* (2013.01)

(56) References Cited

U.S. PATENT DOCUMENTS

| | | | | |
|---|---|---|---|---|
| 3,977,972 | A * | 8/1976 | Bloch | B01D 19/0005 508/111 |
| 4,409,102 | A | 10/1983 | Tanner | |
| 5,766,519 | A | 6/1998 | Erickson | |
| 5,971,371 | A * | 10/1999 | Cheng | B01F 3/04262 261/106 |
| 6,391,093 | B1 * | 5/2002 | French | B23K 26/1435 95/214 |
| 6,616,733 | B1 * | 9/2003 | Pellegrin | B01D 47/04 95/150 |
| 7,264,231 | B2 * | 9/2007 | Kojima | B01D 53/84 261/79.2 |
| 7,815,171 | B2 * | 10/2010 | Raynal | B01D 53/1456 261/76 |
| 8,182,576 | B2 | 5/2012 | Roe et al. | |
| 8,425,665 | B2 * | 4/2013 | Duesel, Jr. | B01D 53/18 95/226 |
| 8,808,497 | B2 * | 8/2014 | Duesel, Jr. | B01D 1/14 159/16.1 |
| 8,865,453 | B2 * | 10/2014 | Augenstein | B01D 53/85 435/266 |
| 9,005,337 | B2 | 4/2015 | Grill | |
| 9,617,509 | B2 * | 4/2017 | Li | C12M 29/02 |
| 2006/0039853 | A1 * | 2/2006 | Fan | B01D 53/62 423/637 |
| 2006/0144229 | A1 | 7/2006 | Kalmari | |
| 2006/0213370 | A1 | 9/2006 | Leonard et al. | |
| 2010/0107872 | A1 | 5/2010 | Bethell | |
| 2011/0263009 | A1 * | 10/2011 | Vellinga | C12M 29/06 435/297.1 |
| 2012/0216680 | A1 * | 8/2012 | Vimalchand | B01D 53/62 96/242 |
| 2012/0238793 | A1 | 9/2012 | Cullinane et al. | |
| 2013/0260443 | A1 | 10/2013 | Varani et al. | |
| 2014/0329299 | A1 | 11/2014 | Guenther | |
| 2015/0352463 | A1 * | 12/2015 | Grave | C07C 7/11 203/14 |

OTHER PUBLICATIONS

Extended European Search Report dated Apr. 5, 2019; Application No. 16842678.1-1104 / 3341110 PCT/US2016048951—(9) pages.
Margareta Persson, Evaluation of Upgrading Techniques for Biogas, Nov. 2003, Swedish Gas Center, Report SGC 142.

* cited by examiner

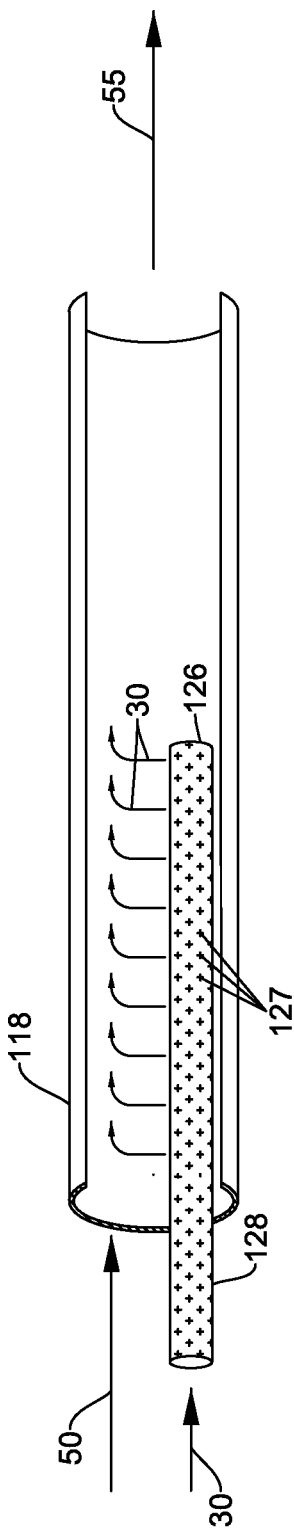
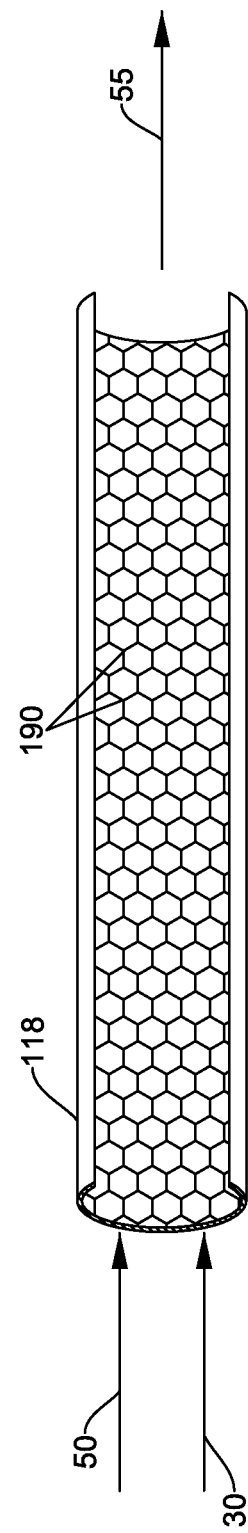

METHOD AND APPARATUS FOR TREATING BIOGAS

CROSS-REFERENCE TO RELATED APPLICATIONS

This application is a continuation-in-part of, and claims priority to, U.S. Ser. No. 15/248,510, filed Aug. 26, 2016 which, in turn, claims priority to U.S. provisional application Ser. No. 62/211,494, filed Aug. 28, 2015, the entire contents of each application is incorporated herein by reference.

BACKGROUND OF THE INVENTION

The subject matter disclosed herein relates to a system for use in treating biogas and, more specifically, for a system to perform a separation process on biogas by which carbon dioxide is separated from methane in the biogas.

As is known in the art, biogas is produced from anaerobic digestion and contains primarily methane and carbon dioxide with lesser quantities of other constituents. Methane may be present in an amount ranging from fifty to sixty-five percent (50-65%) by volume, carbon dioxide may be present in an amount ranging from thirty-five to fifty percent (35-50%) by volume, and the other constituents may include small percentages of nitrogen, oxygen, hydrogen sulfide, and other trace constituents.

As is also known in the art, it is desirable to separate the methane from the carbon dioxide along with other constituents to obtain a purified gas that may be used as a natural gas substitute. Several processes exist by which the methane can be separated from the biogas including, for example, a water wash process, chemical absorption, pressure swing absorption, and membrane separation.

During the water wash process, biogas is injected into water relying on the fact that carbon dioxide and hydrogen sulfide are many times more soluble in water than methane. The process typically occurs at an elevated pressure and reduced temperature to enhance the solubility of carbon dioxide and hydrogen sulfide in water. Historically, tall vessels have been constructed in which water is pumped into the top of the vessel and the biogas is pumped into the bottom of the vessel. As the biogas rises through the water, the carbon dioxide, hydrogen sulfide, and other water soluble trace constituents are absorbed into the water. Because the process is typically performed at an elevated pressure and at a lower temperature, the water and/or biogas is often chilled and/or compressed prior to entry into the vessel.

However, such systems have several drawbacks. The height of the vessels is substantial in order to provide sufficient time for the biogas to be in contact with the water and for the carbon dioxide to be absorbed by the water. Further, the material from which the vessel is made must be corrosion resistant due to the presence of hydrogen sulfide in the biogas and due to carbonic acid formation from the carbon dioxide released during the process. The vessels are, therefore, typically constructed of stainless steel. The size and materials of the vessel as well as the volume of water within the vessels result in a substantial amount of weight for each vessel. Consequently, the water wash treatment vessel requires a substantial physical foundation as well. The physical construction of the system as well as the materials from which the system are constructed are significant capital expenditures for a water wash treatment facility. Thus, it would be desirable to provide an improved system and method for performing the water wash process.

BRIEF DESCRIPTION OF THE INVENTION

The subject matter disclosed herein describes an improved system and method for performing a water wash process on a biogas supply. Multiple risers are provided to perform different steps in the water wash process. In an initial step, carbon dioxide along with other soluble constituents are absorbed from the biogas stream. For the purposes of describing the water wash process herein, references to removing carbon dioxide from the biogas stream may similarly apply to or include removal of the other soluble constituents. The absorption can be performed by utilizing a series of absorption risers. According to one embodiment of the invention, each absorption riser is configured to be installed below grade. The inlets for receiving a biogas stream and a water stream are located at a top end of the riser. The outlets for removing the purified gas stream and mixed water stream are also located at the top end of the riser. The riser may then be located substantially below grade such that the top end is accessible at or just above the ground level.

It is further contemplated that multiple absorption risers are provided. During installation, a trench may be dug and each of the absorption risers inserted into the trench. The trench may then be filled with absorption risers inserted in the trench. Each absorption riser may have a small diameter to facilitate digging of a trench. The diameter may be between about 4 inches and 48 inches for each riser. In one embodiment of the invention, the risers may be connected in series such that the output of one absorption riser is provided as an input to another absorption riser. In this manner, the biogas stream passes through a series of risers having an effective length much longer than a single riser. Each riser may be, for example, about 20 feet in length and the series connection of risers may be 100 feet or greater in length. In another embodiment of the invention, each absorption riser may be connected in parallel. In this manner a portion of the biogas stream is provided to each riser and the carbon dioxide extracted within a single riser. In a parallel connection, one or more of the absorption risers may be disconnected for cleaning or maintenance while allowing at least a portion of the system to continue operation. In still another embodiment of the invention, the absorption risers may be connected in a combination of serial and parallel connections.

In subsequent steps of the water wash process, the mixed water stream may pass through one or more flash risers and/or air stripping risers. Each of the flash and air stripping risers may similarly be configured with each of the inlets and outlets located at a top end of the riser for installation below grade. The flash risers operate to remove methane gas that was either absorbed with or simply exited the absorption riser with the mixed water. The methane recovered from the flash risers is piped back and recirculated through the absorption risers to improve the quality of the purified biogas stream by increasing the percentage of methane recovery from the original biogas stream. The mixed water that remains after the flash riser includes primarily carbon dioxide. This mixed water is then passed to the air stripping risers where the carbon dioxide is removed and the water may be recirculated and used again in the absorption process.

According to one embodiment of the invention, a system for separating gaseous mixtures from a biogas stream is disclosed. The system includes a plurality of absorption risers where each absorption riser includes a first inlet operable to receive the biogas stream and a second inlet operable to receive a water stream. Each absorption riser also includes an outer pipe, a first inner pipe, and a second inner pipe. The outer pipe has a first end, a second end, and a first length. The first end of the outer pipe is in fluid communication with the second inlet to receive the water stream, and a first dispersion element is located within the outer pipe and within a first fluid flow path exiting the second inlet to distribute the water stream across an interior section of the outer pipe. The first inner pipe is located within the outer pipe and has a first end, a second end, and a second length. The first end of the first inner pipe is proximate the first end of the outer pipe and is in fluid communication with the first inlet to receive the biogas stream. The first inner pipe extends from the first end of the outer pipe and into the outer pipe for the second length to dispense the biogas stream from the second end of the first inner pipe within the absorption riser, and the second length of the first inner pipe is less than the first length of the outer pipe. A second dispersion element is positioned within the outer pipe and located in a second fluid flow path exiting the second end of the first inner pipe to distribute the biogas stream across the interior section of the outer pipe. Each absorption riser also includes a first outlet and a second outlet. The first outlet is in fluid communication with the first end of the outer pipe to receive the biogas stream and to deliver a purified biogas stream from the absorption riser. The second inner pipe is located within the outer pipe and has a first end, a second end, and a third length. The first end of the second inner pipe is proximate the first end of the outer pipe and the second inner pipe extends from the first end of the outer pipe and into the outer pipe for the third length. The third length of the second inner pipe is less than the first length of the outer pipe and greater than the second length of the first inner pipe. The second end of the second inner pipe is operative to receive a mixed water stream, and the second outlet is located at the first end of the second inner pipe and is in fluid communication with the second end of the second inner pipe to deliver the mixed water stream from the absorption riser.

According to another aspect of the invention, each outer pipe is located below grade and the first end of the outer pipe for each of the plurality of absorption risers is located at or above grade, such that each of the first and second inlets and the first and second outlets are at or above grade. Alternately, the outer pipe may be located above grade, and the system may also include an exterior sleeve extending along the first length of the outer pipe and around the outer pipe.

According to still another aspect of the invention, each of the plurality of absorption risers may include a removable packing material inserted within the outer pipe and located in both the first flow path of the water stream and the second fluid flow path of the biogas stream, where the packing material causes each of the first and the second fluid flow paths to mix. The packing material may be a netting material rolled into a coil and inserted within the outer pipe of the absorption riser. Optionally, the packing material may be a mesh material and a bulk material contained within the mesh material.

According to yet other aspects of the invention, a diameter of the outer pipe of each absorption riser may be between 4 inches and 48 inches. The outer pipe of each of the plurality of absorption risers may be made of a polyethylene material, and the outer pipe of each of the plurality of absorption risers may be configured to receive the biogas stream at a pressure of at least ten pounds per square inch gauge.

According to another embodiment of the invention, a method for separating gaseous mixtures from a biogas stream is disclosed. The biogas stream is supplied to at least one absorption riser. Each absorption riser includes an outer pipe having a first end and a second end, and the biogas stream enters each of the absorption risers via a first inlet proximate the first end of the outer pipe. A water stream is supplied to each absorption riser. Each absorption riser includes a second inlet operable to receive the water stream, and the second inlet is proximate to and in fluid communication with the first end of the outer pipe. The water stream is passed over a first dispersion element to distribute the water stream across an interior section of the outer pipe, and the first dispersion element is located within the outer pipe and within a first fluid flow path of the water stream exiting the second inlet. The biogas stream is distributed within the interior section of the outer pipe along a second fluid flow path. The first fluid flow path is mixed with the second fluid flow path to generate a purified biogas stream and a mixed water stream, and the purified biogas stream is dispensed from a first outlet located at either the first end or the second end of the outer pipe. The mixed water stream is dispensed from a second outlet located at either the first end or the second end of the outer pipe, where the first and second outlets are at the same end of the outer pipe.

According to another aspect of the invention, the step of distributing the biogas stream within the interior section of the outer pipe may include transmitting the biogas stream from the first inlet through an inner pipe located within the outer pipe, where the inner pipe has a first end, a second end, a length, and a wall extending for the length of the inner pipe between the first end and the second end and dispensing the biogas stream via a plurality of openings extending through the wall along the length of the inner pipe. The first outlet and the second outlet are both located at the second end of the outer pipe.

According to still another aspect of the invention, the step of distributing the biogas stream within the interior section of the outer pipe may include transmitting the biogas stream from the first inlet through a first inner pipe located within the outer pipe, where the first inner pipe has a first end, a second end, a length, and a wall extending for the length of the first inner pipe between the first end and the second end. The first end of the first inner pipe is proximate the first end of the outer pipe and the biogas stream is dispensed from the second end of the first inner pipe. The biogas stream may be passed over a second dispersion element located within the outer pipe and located within a second fluid flow path of the biogas stream exiting the second end of the first inner pipe to distribute the biogas stream across the interior section of the outer pipe. The step of dispensing the mixed water stream from a second outlet may include the step of receiving the mixed water stream at a second end of a second inner pipe, where the second inner pipe having a first end, opposite the second end, and a length. The first end of the second inner pipe is proximate the first end of the outer pipe, the second outlet is in fluid communication with the first end of the second inner pipe, and the first outlet and the second outlet are both located at the first end of the outer pipe.

According to yet another embodiment of the invention, a system for separating gaseous mixtures from a biogas stream is disclosed. The system includes at least one absorption riser having a first end and a second end. Each absorption riser includes a first inlet operable to receive the biogas stream and a second inlet operable to receive a water stream.

The first inlet and the second inlet are both located at the first end of the absorption riser. Each absorption riser also includes an outer pipe having a first end and a second end, where the first end is proximate the first end of the absorption riser and is in fluid communication with the second inlet to receive the water stream. At least one dispersion element is located within the outer pipe and in a first fluid flow path exiting the second inlet to distribute the water stream across an interior section of the outer pipe. A first outlet is operable to deliver a purified biogas stream from the absorption riser, and a second outlet is operable to deliver a mixed water stream from the absorption riser. The first outlet and the second outlet are both located at either the first end or the second end of the absorption riser.

According to another aspect of the invention, an inner pipe may be located within the outer pipe, where the inner pipe has a first end, a second end, a length, and a wall extending for the length of the inner pipe between the first end and the second end. The first end of the inner pipe is proximate the first end of the outer pipe and is in fluid communication with the first inlet to receive the biogas stream. The inner pipe extends from the first end of the outer pipe and into the outer pipe for the length of the inner pipe and the inner pipe further includes a plurality of openings extending through the wall and distributed along the length of the inner pipe to dispense the biogas stream from the inner pipe into the water stream within the absorption riser. The first outlet and the second outlet are both located at the second end of the absorption riser.

According to still another aspect of the invention, a first inner pipe and a second inner pipe may be located within the outer pipe. The first inner pipe has a first end and a second end where the first end of the first inner pipe is proximate the first end of the outer pipe and is in fluid communication with the first inlet to receive the biogas stream. The first inner pipe extends from the first end of the outer pipe and into the outer pipe for a length to dispense the biogas stream from the second end of the first inner pipe within the absorption riser. A second dispersion element may be positioned within the outer pipe and located in a second fluid flow path exiting the second end of the first inner pipe to distribute the biogas stream across the interior section of the outer pipe. The second inner pipe has a first end and a second end, where the first end of the second inner pipe is proximate the first end of the outer pipe and the second inner pipe extends from the first end of the outer pipe and into the outer pipe for a length greater than the length of the first inner pipe. The second end of the second inner pipe is operative to receive a mixed water stream, and the first outlet and the second outlet are both located at the first end of the absorption riser.

According to another embodiment of the invention, a system for separating gaseous mixtures from a biogas stream includes an outer pipe having a first end, a second end, and a length and an inner pipe within the outer pipe, the inner pipe having a first end, a second end, and a length. The length of the inner pipe is less than the length of the outer pipe, and the first end of the inner pipe is proximate the first end of the outer pipe. The inner pipe extends from the first end of the outer pipe into the outer pipe, and the inner pipe includes multiple perforations distributed along the length of the inner pipe. A first inlet is in fluid communication with the first end of the inner pipe to deliver the biogas stream into the inner pipe, and the biogas stream is dispensed from the inner pipe into the outer pipe via the perforations. A second inlet is in fluid communication with the first end of the outer pipe to deliver a water stream into the outer pipe, and the water stream contacts the biogas stream within the outer pipe to remove carbon dioxide from the biogas stream, resulting in a purified biogas stream and a mixed water stream within the outer pipe. A first outlet is in fluid communication with the second end of the outer pipe to deliver the purified biogas stream from the outer pipe, and a second outlet is in fluid communication with the second end of the outer pipe to deliver the mixed water stream from the outer pipe.

According to another aspect of the invention at least one dispersion element may be mounted within the outer pipe to distribute the flow of at least one of the biogas stream and the water stream within an interior of the outer pipe. A removable packing material may also be inserted within the outer pipe and located in both a first flow path of the water stream and a second flow path of the biogas stream. The packing material causes each of the first and the second flow paths to mix. The packing material may be a netting material rolled into a coil and inserted within the outer pipe. Optionally, the packing material may be a mesh material and a bulk material contained within the mesh material.

According to still another aspect of the invention, the outer pipe may include a first segment, a second segment, and a third segment. The first segment extends from the first end of the outer pipe along a first portion of the length of the outer pipe, the first end of the outer pipe is located at or above grade, and the first segment extends from above grade to below grade. The second segment extends from the first segment along a second portion of the length of the outer pipe and is located below grade. The third segment extends from the second segment to the second end of the outer pipe, and the second end of the outer pipe is located at or above grade and the third segment extends from below grade to above grade. The system also includes a second inner pipe extending from the second end and into the third segment of the outer pipe. The mixed water stream enters the second inner pipe, and the second outlet is in fluid communication with the second inner pipe to deliver the mixed water stream.

According to yet another aspect of the invention, the outer pipe may be arranged in a generally horizontal plane at or above grade. The system may also include a second outer pipe having a first end, a second end, and a length and a second inner pipe having a first end, a second end, and extending within the second outer pipe from the first end of the second outer pipe toward the second end of the second outer pipe. The second end of the outer pipe connects to the second outer pipe proximate the first end of the second outer pipe, and the first outlet and the second outlet are the second end of the outer pipe. The second outer pipe includes a third outlet at the first end of the second outer pipe to deliver the purified biogas stream from the second outer pipe. The second inner pipe receives the mixed water stream at the second end of the second inner pipe, and the second inner pipe includes a fourth outlet at the first end of the second inner pipe. The fourth outlet extends through the first end of the second outer pipe to deliver the mixed water stream from the second outer pipe.

According to still another aspect of the invention, a polishing tank is in fluid communication with the first outlet to receive the purified biogas stream from the outer pipe, and a polishing agent is located within the polishing tank. The polishing agent is selected to remove residual carbon dioxide from the purified biogas stream and may be a hydroxide compound.

According to still another embodiment of the invention, a method for separating gaseous mixtures from a biogas stream is disclosed. The biogas stream is supplied to a first inlet in fluid communication with an inner pipe, and a water stream is supplied to a second inlet in fluid communication with an outer pipe. The outer pipe has a first end, a second end, and a length, and the inner pipe has a first end, a second end, and a length less than the length of the outer pipe. The first end of the inner pipe is proximate the first end of the outer pipe. The first inlet is in fluid communication with the first end of the inner pipe, and the second inlet is in fluid communication with the first end of the outer pipe. The biogas stream is delivered from the inner pipe to the outer pipe via multiple perforations distributed along the length of the inner pipe. The biogas stream is mixed with the water stream within the outer pipe to remove carbon dioxide from the biogas stream, resulting in a purified biogas stream and a mixed water stream within the outer pipe. The purified biogas stream is dispensed from a first outlet located at the second end of the outer pipe, and the mixed water stream is dispensed from a second outlet located at the second end of the outer pipe.

According to yet another embodiment of the invention, a system for separating gaseous mixtures from a biogas stream includes an absorption riser having a first end and a second end and a polishing tank. The absorption riser includes a first inlet operable to receive the biogas stream, and a second inlet operable to receive a water stream. The first inlet and the second inlet are both located at the first end of the absorption riser, and the water stream contacts the biogas stream within the absorption riser to remove carbon dioxide from the biogas stream, resulting in a purified biogas stream and a mixed water stream within the absorption riser. A first outlet is operable to deliver the purified biogas stream from the absorption riser, and a second outlet is operable to deliver the mixed water stream from the absorption riser. The first outlet and the second outlet are both located at the second end of the absorption riser. The polishing tank is in fluid communication with the first outlet to receive the purified biogas stream from the absorption riser. A polishing agent is located within the polishing tank, where the polishing agent is selected to remove residual carbon dioxide from the purified biogas stream.

These and other objects, advantages, and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWING(S)

Various exemplary embodiments of the subject matter disclosed herein are illustrated in the accompanying drawings in which like reference numerals represent like parts throughout, and in which:

FIG. 18 is a partial sectional view of the horizontal absorption riser of FIG. 15 according to one embodiment of the invention;

FIG. 19 is a partial sectional view of the horizontal absorption riser of FIG. 15 according to another embodiment of the invention;

Figure 1:
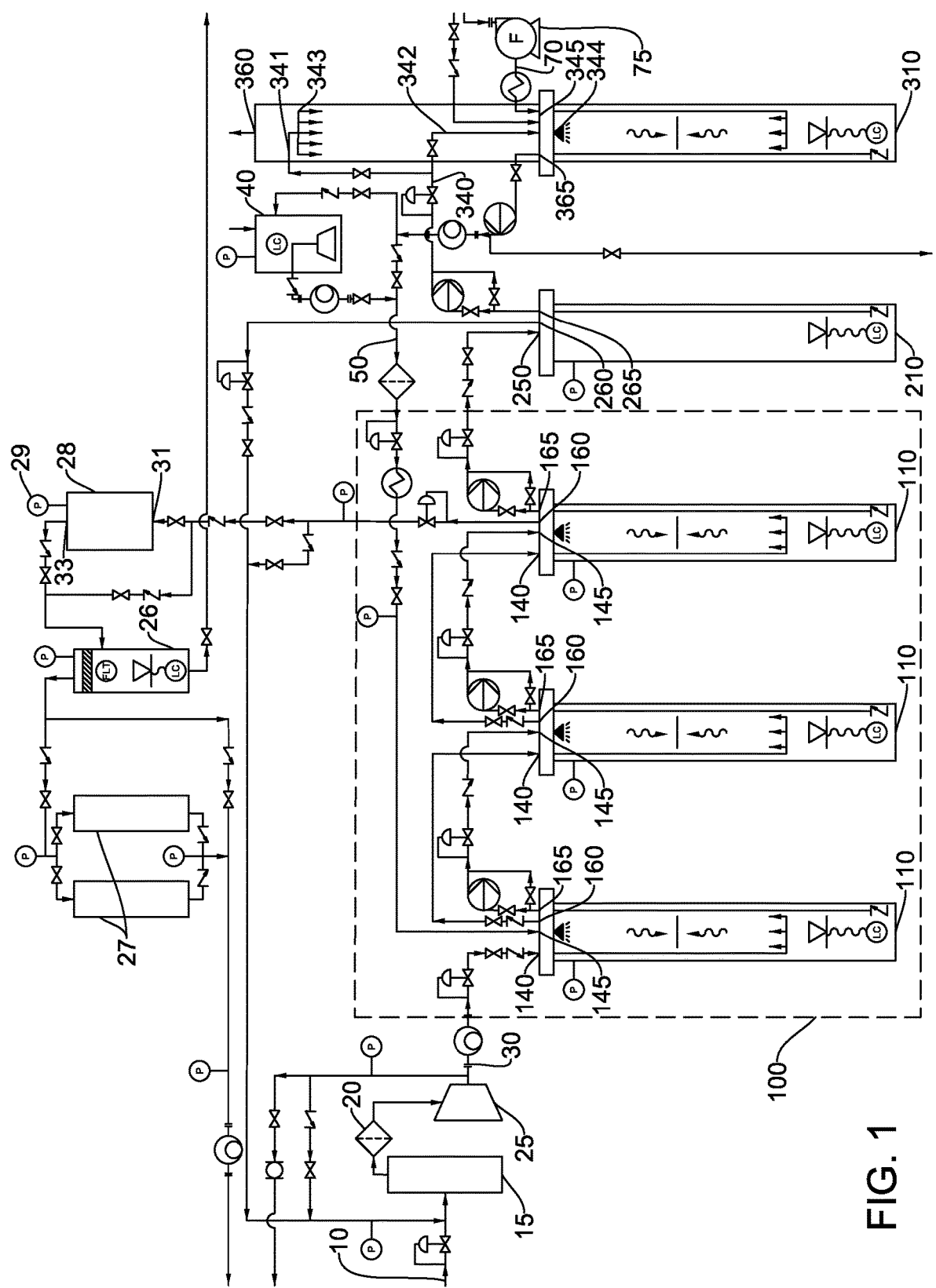
FIG. 1 is a schematic representation of an exemplary biogas treatment system incorporating one embodiment of the present invention.

In describing the preferred embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terms similar thereto are often used. They are not limited to direct connection but include connection through other elements where such connection is recognized as being equivalent by those skilled in the art.

DETAILED DESCRIPTION OF THE PREFERRED EMBODIMENTS

The various features and advantageous details of the subject matter disclosed herein are explained more fully with reference to the non-limiting embodiments described in detail in the following description.

Turning initially to FIG. 1, an exemplary biogas treatment system incorporating one embodiment of the present invention is illustrated. A biogas stream 10 is provided as an input to the system, where the biogas may be produced, for example, from an anaerobic decomposition process. The anaerobic decomposition process may, for example, convert food waste, sewage, animal manure, landfill waste and the like into biogas. The biogas primarily includes methane and carbon dioxide with a lesser percentage of other constituents, such as nitrogen, oxygen, and hydrogen sulfide. Methane is typically present in a concentration of fifty to sixty-five percent (50-65%) by volume and carbon dioxide is typically present in a concentration of thirty-five to fifty-five percent (35-50%) by volume. The disclosed water wash process employed by the biogas treatment system removes the carbon dioxide and other trace constituents, such as hydrogen sulfide and siloxanes, resulting in a purified biogas stream having a methane content of ninety to ninety-eight percent (90-98%) and carbon dioxide content to as low as about one percent (1%). The resulting purified biogas stream may be used as a replacement fuel for natural gas that can include the use in a compressed natural gas engine. Although the invention will be discussed with respect to a water wash process for treating biogas, it is understood that the system may be used to treat other gas mixtures in which the relative solubility of one gas in the mixture is substantially higher than the other gas in the mixture.

Some initial processing of the biogas stream may occur prior to supplying the biogas stream to the water wash system. An optional hydrogen sulfide removal process 15 such as an iron sponge type system may be inserted in series with the biogas stream 10 to perform an initial removal of hydrogen sulfide present in the biogas stream. Because hydrogen sulfide is corrosive, removal of the gas at an initial stage limits the effects of the gas on the system components through the water wash process. Optionally, hydrogen sulfide may be removed in the off-gas exhaust output from the stripping process. The biogas stream may also be passed through a filter 20 to remove particulate content. In addition, carbon dioxide has increased solubility characteristics with decreasing temperature and increasing pressure. The biogas stream is, therefore, passed through a compressor 25 to achieve an elevated pressure. The pressure range of the compressed biogas stream 30 may be between forty and two hundred pounds per square inch gauge (40-200 psig). According to one embodiment of the invention, the pressure range of the compressed gas is between about one hundred and one hundred fifty pounds per square inch gauge (100-150 psig). The compressed biogas may also be chilled, for example, to between thirty-five and sixty-eight degrees Fahrenheit (35-68° F.). The compressed and/or chilled biogas stream 30 is provided as an input to the water wash process.

The water wash process utilizes water to remove the carbon dioxide from the biogas stream. According to the illustrated embodiment, water is provided to a holding tank 40 from which a water stream 50 is provided to the water wash process. Water provided to the holding tank 40 may be chilled and/or under pressure to facilitate the water wash process. Optionally, the holding tank 40 may incorporate a chiller and/or a compressor to chill or pressurize the water prior to supplying it in the water stream. The water, for example, may be chilled to between thirty-five and sixty-eight degrees Fahrenheit (35-68° F.) and pressurized to mix with the compressed biogas stream 30 at about the same input pressure of the compressed biogas stream. The carbon dioxide has significantly more solubility in water than methane and the solubility is further improved with increased pressure and reduced temperature. Thus, providing a chilled and/or pressurized water stream 50 and a compressed and/or chilled biogas stream 30 into the absorption risers 110 enhance the absorption of carbon dioxide from the biogas and into the water.

Figure 5:
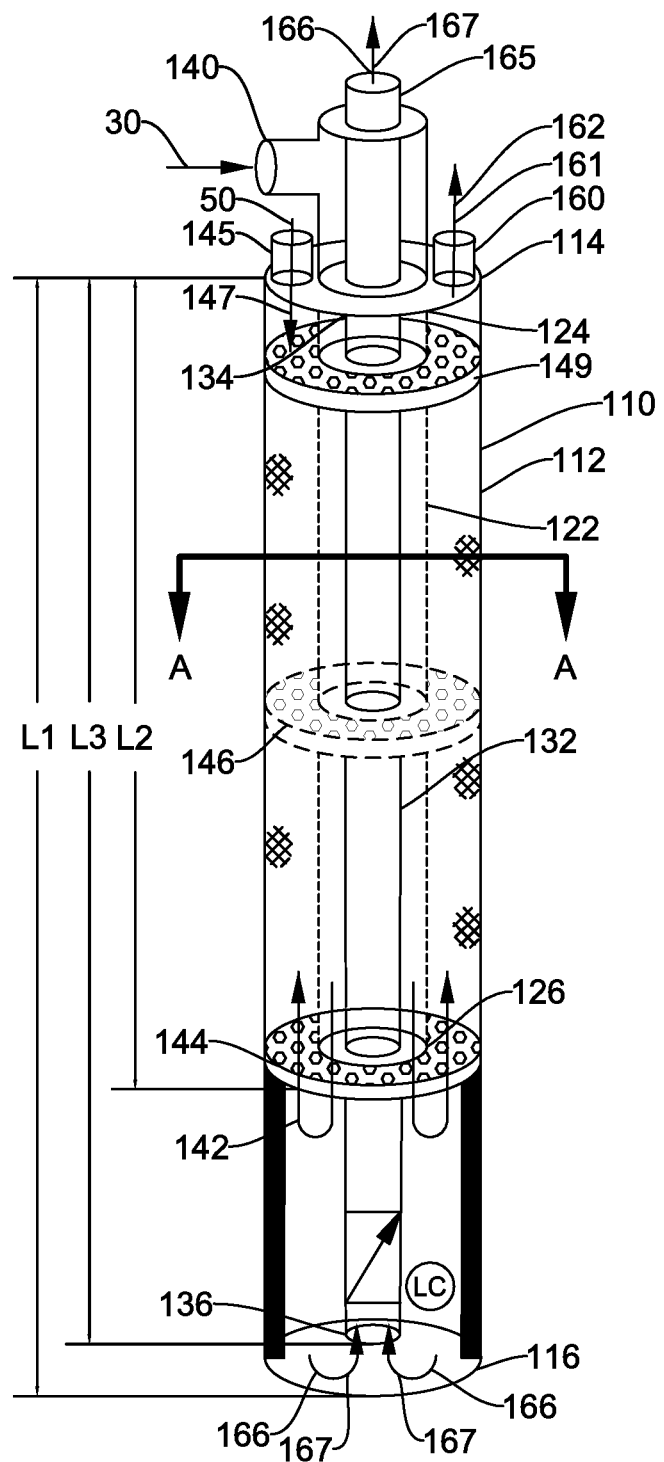
FIG. 5 is a front view of one embodiment of an absorption riser from the biogas treatment system of FIG. 1.

The water wash process begins with an absorption process 100 that has multiple absorption risers 110 operatively connected together to remove the carbon dioxide from the compressed biogas stream 30. Referring also to FIG. 5, each absorption riser 110 includes multiple pipes. In the illustrated embodiment, the absorption riser 110 includes an outer pipe 112, a first inner pipe 122, and a second inner pipe 132. According to the illustrated embodiment, each of the pipes is concentric to the others. Optionally, the first inner pipe 122 and the second inner pipe 132 may be positioned adjacent to each other or extend downward at different locations within the outer pipe 112. The outer pipe 112 has a first end 114, a second end 116, and a first length, L1. The first inner pipe 122 has a first end 124, a second end 126, and a second length, L2. The second inner pipe 132 has a first end 134, a second end 136, and a third length, L3. According to one embodiment of the invention, each of the absorption risers 110 are installed in a vertical orientation, such that the first ends 114, 124, 134 of each pipe 112, 122, 132 are generally positioned at the top of each absorption riser 110. The first inner pipe 122 extends for the second length, L2 into the outer pipe 112 such that the compressed biogas stream 30 may be delivered into a lower segment of the absorption riser 110. According to the illustrated embodiment, the first inner pipe 122 is cylindrical and open at the second end 126. The compressed biogas stream 30 flows from the first inlet 140 and exits at the second end 126 of the first inner piper 122. The second inner pipe 132 extends for the third length, L3, through the first inner piper 122, beyond the second end 126 of the first inner pipe 122, and into the outer pipe 112. The second inner pipe 132 is cylindrical and the second end 136 of the second inner pipe 132 includes a check valve between the interior of the outer pipe 112 and the interior of the second inner pipe 132.

Each absorption riser 110 includes a set of inlets and outlets to allow water and biogas to flow into and out of the riser 110. A first inlet 140 receives the compressed biogas stream 30 and is located on the first end 114 of the outer pipe 112. The first inlet 140 is in fluid communication with the first end 124 of the first inner pipe 122 and establishes a flow path for the compressed biogas stream 30 into the absorption riser 110. The first inner pipe 122 extends into the absorption riser 110 for the length, L2, of the inner pipe 122. According to the embodiment illustrated in FIG. 5, the second end 126 of the first inner pipe 122 terminates at a dispersion element 144 proximate the second end 116 of the first inner pipe 122. A second inlet 145 receives the water stream 50 and is located on the first end 14 of the outer pipe 112. The second inlet 145 is in fluid communication with the first end 114 of the outer pipe 112 to dispense the water stream 50 from the top of the absorption riser 110. As will be discussed in more detail below, the water stream 50 is dispensed at the top of the interior of the absorption riser 110 via the second inlet 145 and the compressed biogas stream 30 is dispensed at the bottom of the interior of the absorption riser 110 via the first inner piper 122, and the compressed biogas stream 30 passes up through the water stream 50 within the absorption riser 110. As the water stream 50 falls to the bottom of the absorption riser 110 it mixes with the biogas stream and the carbon dioxide within the compressed biogas stream 30 is dissolved into the water. Although small amounts of methane may be absorbed in the water, the majority of the methane remains unabsorbed and rises to the top of the absorption riser 110. Because carbon dioxide is removed from the compressed biogas stream 30 as it interacts with the water stream 50, the flow of biogas resulting from mixing with the water will be referred to herein as a purified biogas stream 162. Similarly, because the water stream 50 absorbs carbon dioxide from the compressed biogas stream 30, the resulting water stream will be referred to herein as a mixed water stream 166.

Figure 6:
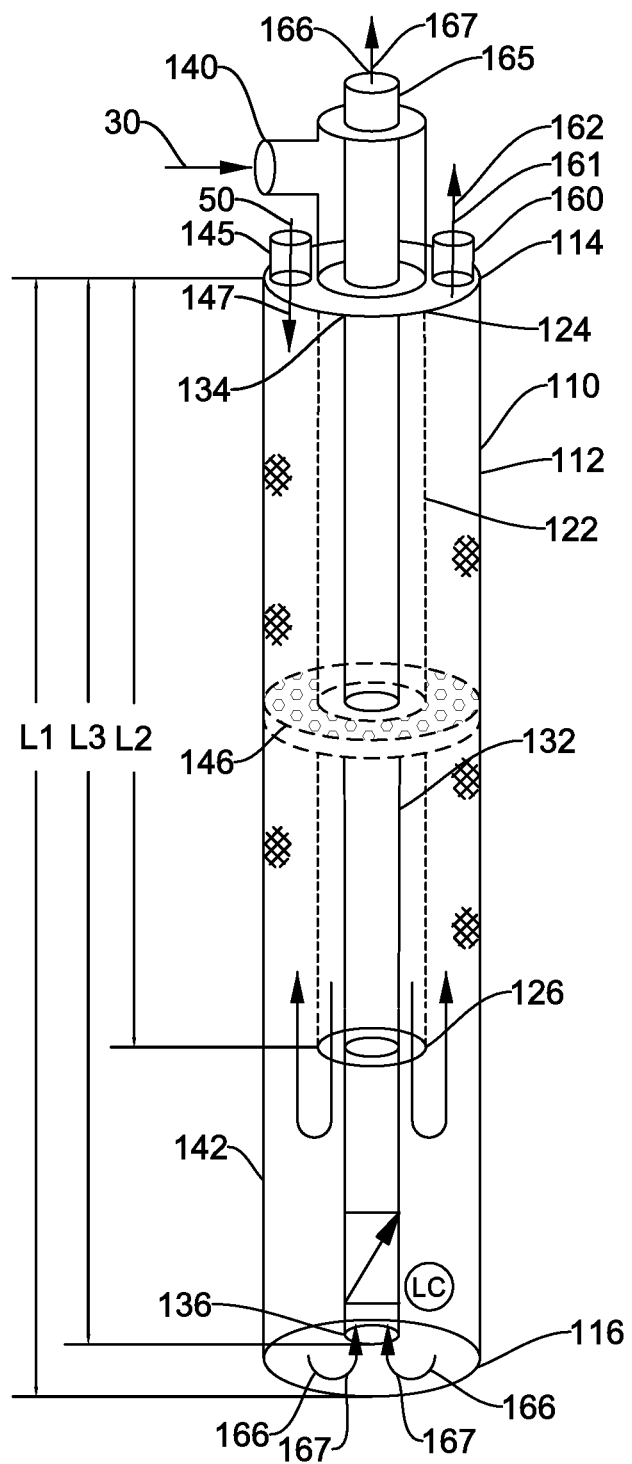
FIG. 6 is a front view of another embodiment of an absorption riser from the biogas treatment system of FIG. 1.
Figure 15:
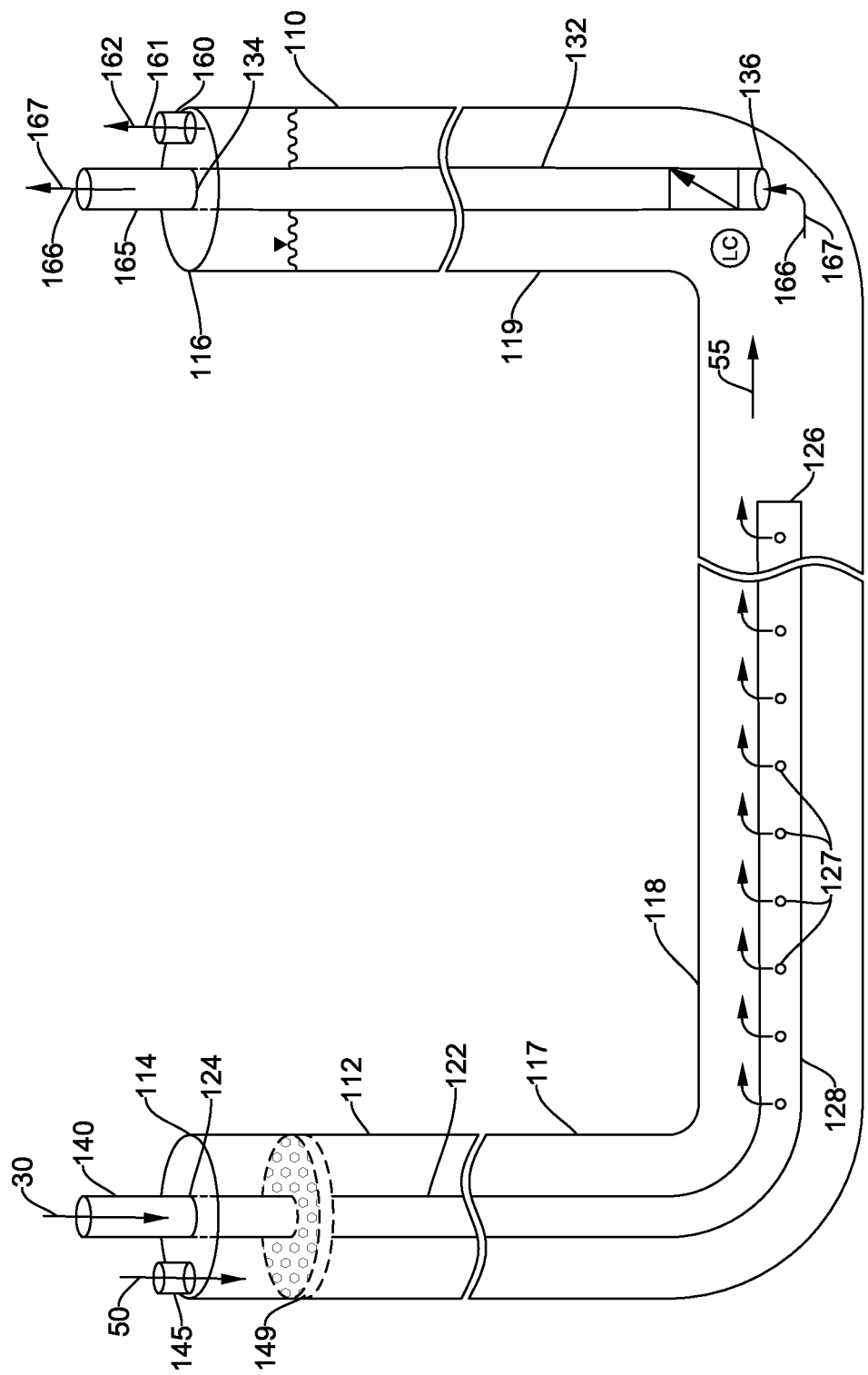
FIG. 15 is a schematic representation of an exemplary biogas treatment system incorporating a horizontal absorption riser according to another embodiment of the present invention.
Figure 16:
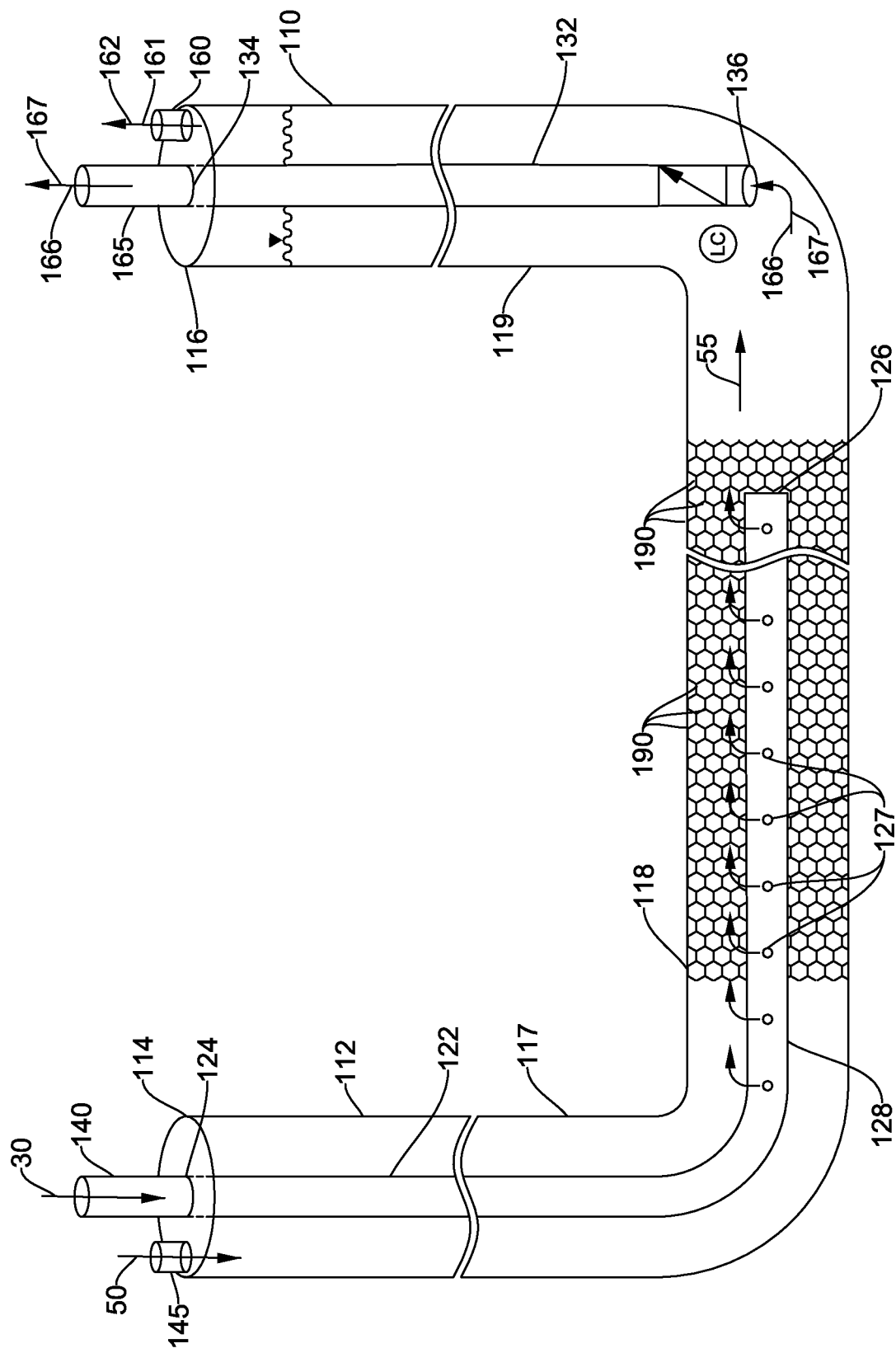
FIG. 16 is a schematic representation of an exemplary biogas treatment system incorporating a horizontal absorption riser according to another embodiment of the present invention.
Figure 17:
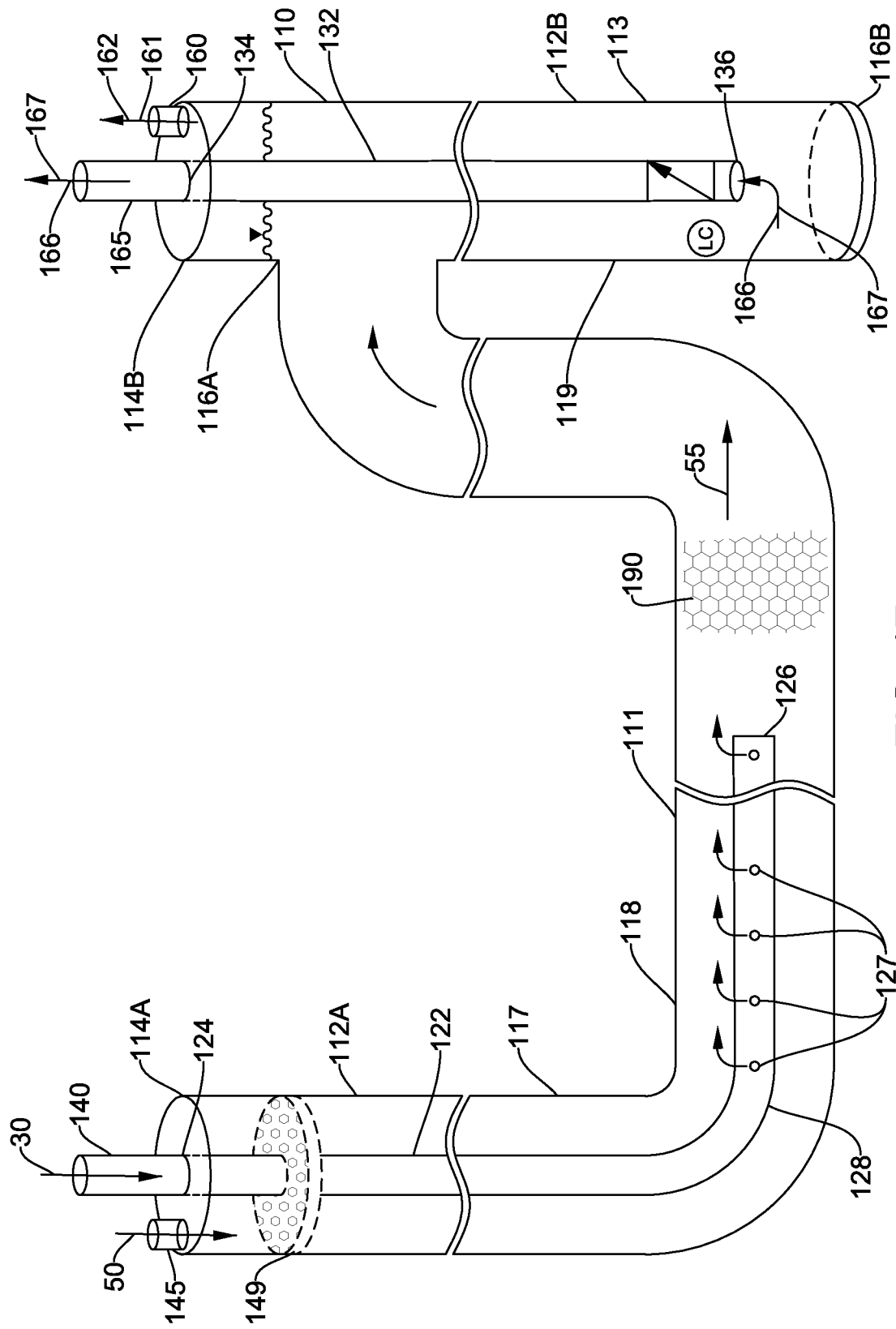
FIG. 17 is a schematic representation of an exemplary biogas treatment system incorporating a horizontal absorption riser according to another embodiment of the present invention.

According to the embodiment illustrated in FIG. 6, the second end 126 of the first inner pipe 122 simply terminates within the outer pipe 112 without a dispersion element 144 located proximate the second end 126 of the first inner pipe 122. The second end 126 of the first inner pipe 122 may be configured to disperse the compressed biogas stream 30 into water flowing within the outer pipe 112. The dispersion may be achieved, for example, via a series of holes 127 located along the length of the first inner pipe 122 as shown in FIGS. 15-17, via a nozzle, or series of nozzles positioned at the second end 126, or via other dispersion methods which are integrally formed with the first inner pipe 122. Optionally, a series of nozzles may be located along the length of the first inner pipe 122, where each nozzle disperses a portion of the biogas stream within the outer pipe 112. According to still another option, multiple inner pipes 122 may be provided, where each inner pipe 122 includes a series of holes 127 or nozzles spaced along the length of each inner pipe 122 to facilitate dispersion of the biogas stream 30 throughout the interior of the outer pipe 112. It is contemplated that an optional dispersion element 146 may still be located within the outer pipe 112 at a location between the inlet of the water stream and the inlet of the compressed biogas stream within the absorption riser 110 if desired for further mixing of the two streams.

A first outlet 160 located at the first end 114 of the outer pipe 112 provides a flow path 161 for the purified biogas stream 162 to exit the absorption riser. The first outlet 160 is in fluid communication with and receives the purified biogas stream 162 from the interior of the outer pipe 112. A second outlet 165 is also located at the first end 114 of the outer pipe 112 and provides a flow path 167 for the mixed water stream 166. The second outlet 165 is in fluid communication with the first end 134 of the second inner pipe 132. The mixed water stream 166 enters the second end 136 of the second inner pipe 132 and travels up through the second inner pipe 132 to the second outlet 165. According to the illustrated embodiment, each of the outer pipe 112, first inner pipe 122, and second inner pipe 132 are concentric about a central axis. The second inner pipe 132 is located within the first inner pipe 122, which is, in turn, located within the outer pipe 112. As discussed above and for purposes of illustration in FIG. 5, the first end 114, 124, 134 of each pipe 112, 122, 132 ends at substantially the same point. It is contemplated that in various embodiments the first end 124, 134 of each of the first inner pipe 122 and the second inner pipe 132 may extend for a short distance beyond the first end 114 of the outer pipe 112 to facilitate connections between each pipe and an inlet or outlet. It is further contemplated that an inlet 140, 145 or outlet 160, 165 may be positioned along and enter the outer pipe 112 via a side wall proximate the end of the absorption riser 110. For example, the first inlet 140 is shown connecting generally orthogonally to a wall of the first inner pipe 122 beyond the first end 114 of the outer pipe and the second inner pipe 132 extends through an end wall of the first inner pipe 122 to connect to the second outlet 165. Alternately, the first inlet 140 or second outlet 165 may include a fixture connected to the first end 114 of the outer pipe 112 and comprise the necessary connections to establish the fluid flow paths from the inlet and outlet to the inner pipes extending into the outer pipe 112.

With reference again to FIG. 5, each absorption riser 110 may also include one or more dispersion elements located within the flow path to facilitate mixing of the compressed gas stream 30 with the water stream 50. A first dispersion element 149 is located in the flow path 147 of the water stream 50 as it exits the second inlet 145, and a second dispersion element 144 is located in the flow path 142 of the compressed gas stream 30 as it exits the second end 126 of the first inner pipe 122. Each dispersion element 144, 149 is operable to distribute either the compressed gas stream 30 or the water stream 50 throughout the interior of the outer pipe 112. According to the illustrated embodiment, each dispersion element 144, 149 is a diffuser plate, where the diffuser plate extends around the first inner pipe 122, forming a disk within the interior or the outer pipe 112. The diffuser plate includes multiple holes extending through the plate which allow the water and gas to flow through. The holes are distributed around the surface of the disk such that water and gas flow through and are distributed throughout the interior of the outer pipe 112.

With reference again to FIG. 6, it is contemplated that one or more of the dispersion elements are optionally included within the absorption riser. It is contemplated that other methods of distributing the compressed gas stream 30 and/or the water stream 50 within the absorption riser may be utilized without deviating from the scope of the invention. For example, one or more sparging tubes may be operatively connected to the second inlet 145 or to the second end 126 of the first inner pipe 122 and arranged within the interior of the outer pipe 112 to distribute the water and gas throughout the interior of the outer pipe 112. According to still another embodiment, spray nozzles may be operatively connected to the second inlet 145 or to the second end 126 of the first inner pipe 122 to discharge the water and gas as a mist throughout the interior of the outer pipe 112. An additional dispersion element 146, may be included within the combined streams if desired for further mixing of the water stream 50 with the compressed gas stream 30. According to still other embodiments, various combinations of dispersion elements may be utilized. Each dispersion element distributes the water and gas in finer jets, flows, or droplets to increase the surface area of water and gas present within the outer pipe 112. The increased surface area of water and gas increases the area at which the water and gas may contact each other and thereby increasing the area across which carbon dioxide may transfer from the compressed biogas stream 30 to the water stream 50.

Figure 9:
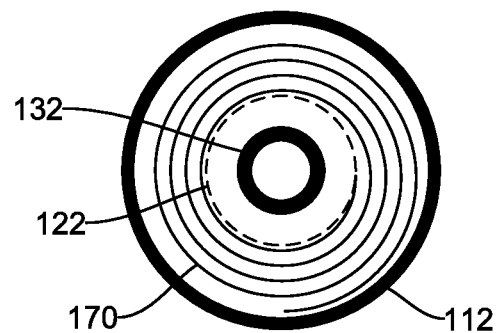
FIG. 9 is a sectional view of the absorption riser of FIG. 5 taken at A-A' illustrating one embodiment of a packing material incorporated into the absorption riser.
Figure 10:
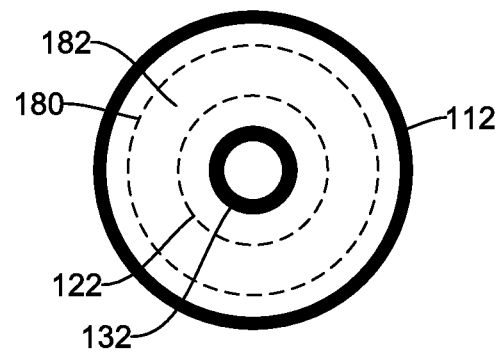
FIG. 10 is a sectional view of the absorption riser of FIG. 5 taken at A-A' illustrating another embodiment of a packing material incorporated into the absorption riser.

It is further contemplated that each absorption riser may include packing material within at least a portion of the interior of the outer pipe 112 to further enhance the mixing of the compressed biogas stream 30 with the water stream 50. In FIG. 5, an additional dispersion plate 146 is shown. One or more additional dispersion plates 146 may be distributed along the length of the interior of the outer pipe 112 to continually redistribute the gas and water as they travel through the interior of the pipe. With reference also to FIGS. 9 and 10, other packing material may be inserted into the outer pipe 112. In FIG. 9, a flexible material 170 is rolled into a coil and inserted between the inner periphery of the outer pipe 112 and the outer periphery of the first inner pipe 122. According to one embodiment of the invention, the flexible material 170 is a netting material, such as a geonet, including multiple holes throughout the material. As the water and gas pass through the absorption riser 110, the netting and the multiple holes create numerous flow paths and opportunities for collisions and, thereby, increasing contact surface area between the water and biogas for transfer of the carbon dioxide from the biogas to the water. In FIG. 10, a mesh material 180 may be formed into a basket or bag and is used to contain another bulk material 182 within the mesh. The bulk material is preferably a material that allows the water and gas to flow through while increasing contact between the water and gas. Optionally, the bulk material may be a medium that has absorptive characteristics such as activated carbon or zeolites which may further aid in the removal of trace constituents from the compressed biogas stream 30. The mesh and bulk materials 180, 182 may be inserted into and removed from the interior of the outer pipe 112 as a unit. Both the flexible material 170 and the mesh and bulk material combination 180, 182 facilitate cleaning of the packing material. The flexible material 170 may be removed and unrolled for cleaning. The mesh and bulk material 180, 182 may be pulled out of the outer pipe 112 and the bulk material spread out for cleaning. Once clean, the flexible material 170 may be rolled back into a coil and inserted back into the outer pipe 112. Similarly, the bulk material 182 may be placed back into the mesh material 180 and inserted into the outer pipe 112.

With reference again to FIG. 1, it is contemplated that multiple absorption risers 110 may be connected in series. The effect of connecting the absorption risers 110 in series is to create an overall longer length of pipe greater than the length of a single riser through which the compressed biogas stream 30 interacts with the water stream 50, allowing for a greater concentration of carbon dioxide to be transferred from the compressed biogas stream 30 to the water stream 50. One of the absorption risers 110 is designated as an initial absorption riser in the system and receives the initial input of the compressed biogas stream at the first inlet 140 and the water stream 50 at the second inlet 145. The first outlet 160 of the initial absorption riser is connected to the first inlet 140 of another absorption riser 110 and the second outlet 165 of the initial absorption riser is connected to the second inlet 145 of the other absorption riser 110. This sequence of connections repeats for each absorption riser in the system until a final absorption riser is reached. At the final absorption riser, the first inlet 140 still receives the biogas stream from the first outlet 160 of the preceding absorption riser and the second inlet 145 receives the water stream from the second outlet 165 of the preceding riser. However, the first outlet 160 of the final absorption riser provides the purified biogas stream 162 and the second outlet 165 of the final absorption riser provides the mixed water stream 166. As the biogas and water streams progress through each absorption riser, the concentration of carbon dioxide in the biogas stream is incrementally reduced and the concentration of carbon dioxide in the water stream is incrementally increased from the starting level at the initial absorption riser to the final levels at the final absorption riser.

Figure 2:
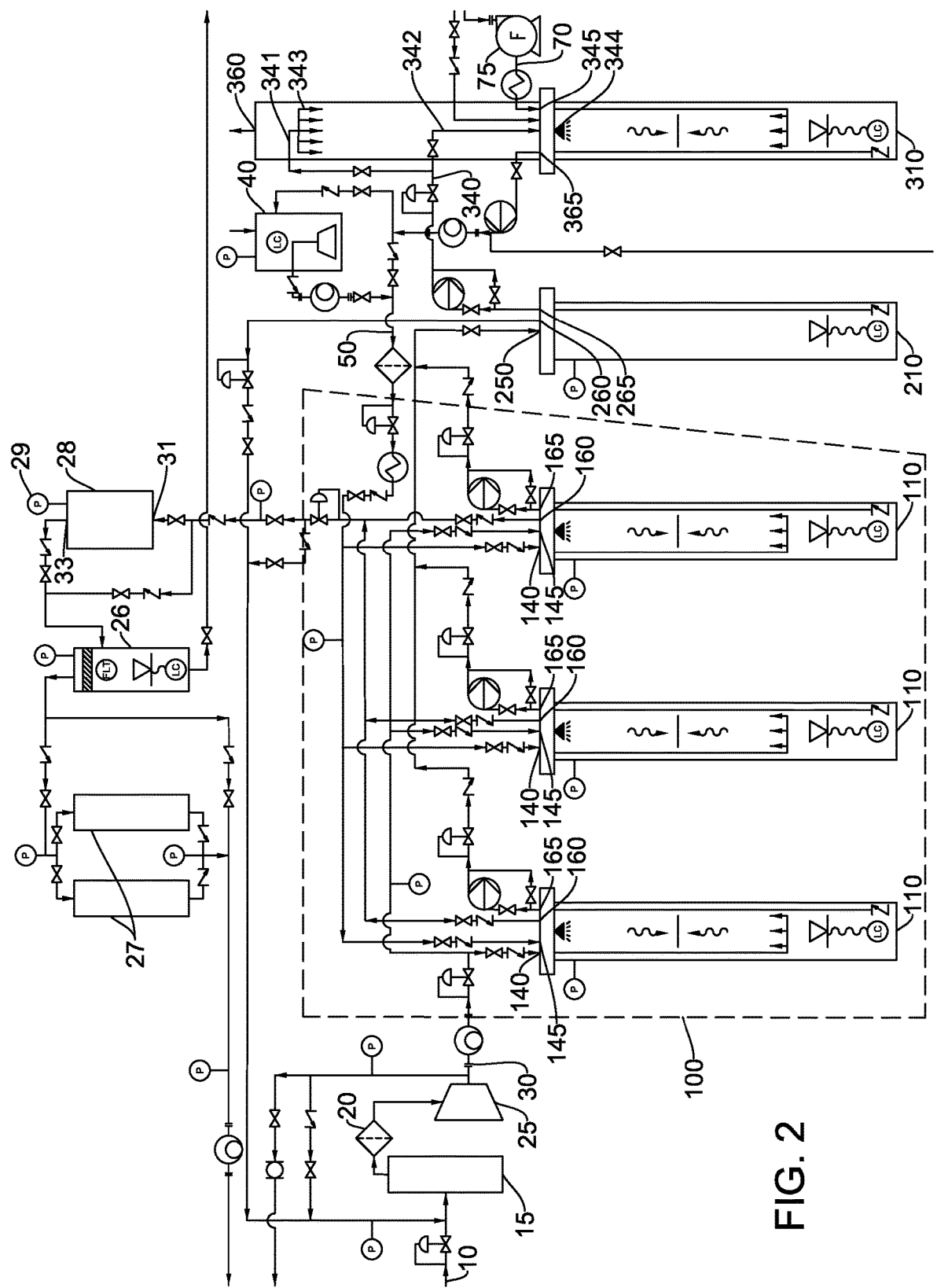
FIG. 2 is a schematic representation of an exemplary biogas treatment system incorporating another embodiment of the present invention.

With reference next to FIG. 2, it is also contemplated that multiple absorption risers 110 may be connected in parallel. Each of the compressed biogas stream 30 and the water stream 50 are split and portions of each stream are supplied to each riser. As illustrated, the compressed biogas stream 30 is provided to the first inlet 140 of each absorption riser 110, and the water stream 50 is provided to the second inlet 145 of each absorption riser 110. The first outlet 160 of each absorption riser is connected to a junction at which the purified biogas stream 162 from each absorption riser is combined and delivered from the system. Similarly, the second outlet 165 of each absorption riser is connected to a second junction at which the mixed water stream 166 from each absorption riser is combined and may be transferred for further processing. To achieve comparable purifying performance to the serial connection discussed above, the volume of biogas introduced into each absorption riser 110 may be split between each absorption riser while the volume of water introduced into each riser remains the same. Thus, a greater volume of water per unit is available for interaction with the same volume of biogas, allowing a greater percentage of the carbon dioxide to be removed in a single absorption riser than when the entire flow of biogas enters a single riser.

According to still another aspect of the invention, it is contemplated that the absorption risers 110 may be connected in a combination of serial and parallel connections. For example, two or three absorption risers 110 may be connected in series as a set of absorption risers with multiple sets of absorption risers connected in parallel. Alternately, the biogas stream 30 may enter a first absorption riser 110 and pass through subsequent absorption risers in series and the water stream 50 may be supplied to the absorption risers in parallel, thereby maximizing the transfer of carbon dioxide from the biogas stream to the water stream at each riser.

In addition to determining whether to connect the absorption risers 110 in series or parallel, a number of other design criteria are considered when configuring the water wash system. As previously discussed, the gas and/or water stream may be cooled or compressed. Further, the diameter and length of each absorption riser 110 is evaluated. In addition, the material from which the absorption riser is constructed must be determined.

Existing water wash systems typically utilize a single stainless steel vessel with a height ranging from twenty to sixty feet and a diameter up to six feet. The size of the vessel, the materials from which it is constructed and the weight of the water and biogas within the vessel further requires structural considerations such as a reinforced concrete footing to support the weight and horizontal stabilization members to prevent tipping.

In contrast, the absorption risers 110 of the present system are constructed from a non-metallic material and, preferably, are constructed of a plastic or reinforced resin material. According to one embodiment of the invention, the risers are made from a polyethylene material, such as high density polyethylene (HDPE) or medium density polyethylene (MDPE), or from a polyimide material. Optionally, the risers may be made from polyvinyl chloride (PVC) or fiberglass. The materials are lighter and less expensive than existing materials, reducing system costs and making construction easier.

Figure 11:
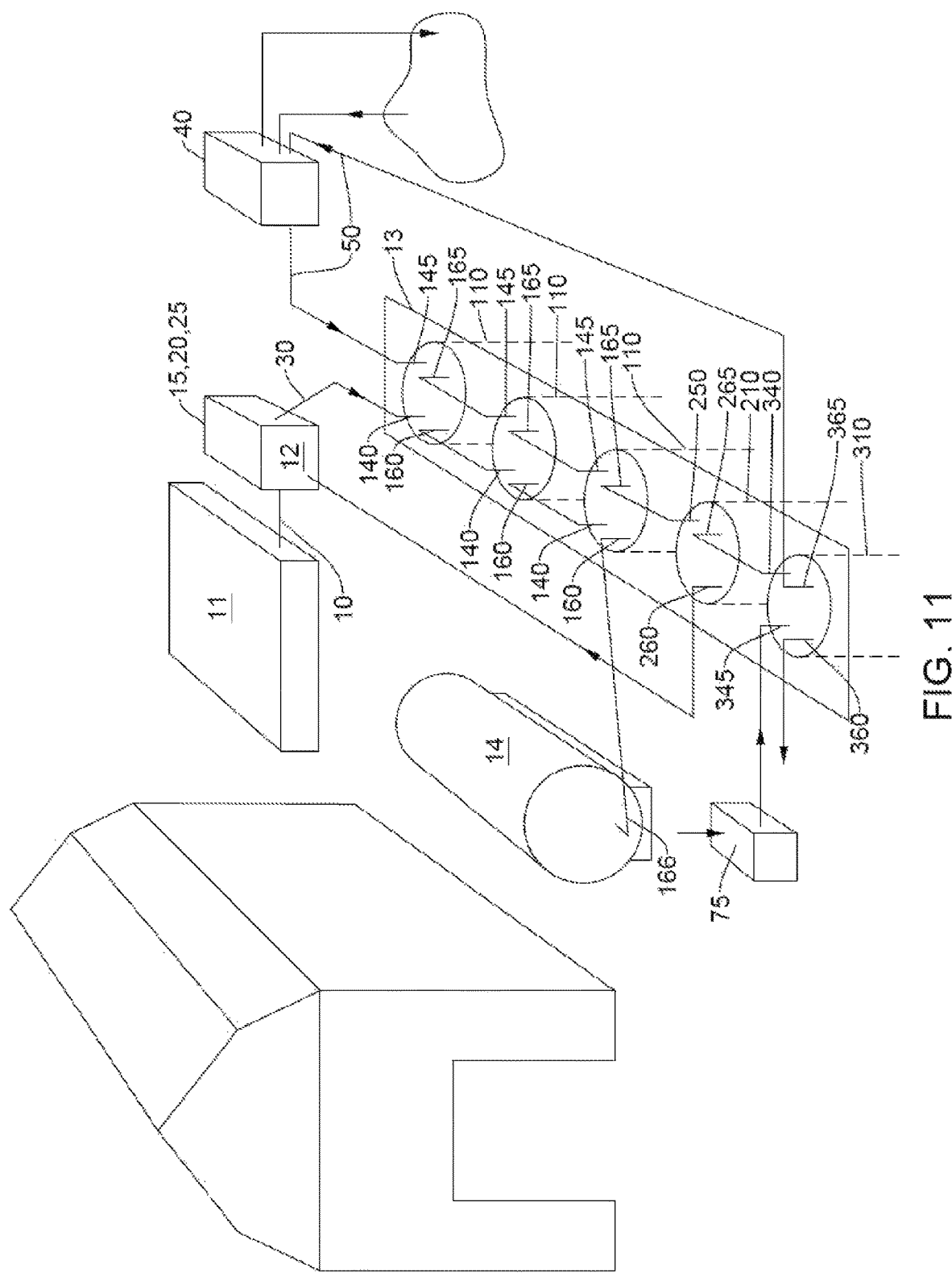
FIG. 11 is an exemplary application incorporating one embodiment of the present invention.

With reference next to FIG. 11, an exemplary installation of one embodiment of the present invention at a farm is illustrated. The farm includes an anaerobic digester 11 to break down animal waste created on the farm. The raw biogas stream 10 output from the anaerobic digester 11 is provided to an initial processing stage 12. With reference also to FIG. 1, the initial processing stage 12 may include the hydrogen sulfide cleaner 15, filter 20, and compressor 25. The initial processing stage, therefore, removes hydrogen sulfide from the raw biogas stream 10 and then filters and compresses the biogas stream, providing a compressed biogas stream 30 to a series of absorption risers 110, a flash riser 210, and an air stripping riser 310.

Each of the risers 110, 210, 310 are installed in a trench 13 and substantially below grade. The diameter of each riser is preferably in the range of four to thirty inches (4-48 in.) and the length may be, for example twenty feet (20 ft.). The trench may be dug using conventional excavation methods and each riser inserted within the trench. Optionally, an auger may be used to drill individual holes into the ground and each riser is inserted into one of the holes. The top of each riser is at or above grade to provide for connection of tubing and fittings for transmitting biogas and/or water to and from each riser. After each riser is installed within the trench 13 or hole, the trench or hole may be back-filled so the earth surrounds each riser. The earth surrounding each riser provides a number of benefits, such as protection from ultraviolet radiation in outdoor installations, insulation for the chilled water, and physical support for each riser when it is filled with biogas and water. In alternate embodiments of the invention, it is contemplated that the risers may be installed below grade, above grade, or a combination thereof. When either a portion or all of a riser is installed above grade, it is contemplated that one or more exterior sleeves may cover the portion of the riser above grade. Each sleeve may provide ultraviolet (UV) ray protection, insulation, support, or a combination thereof for the portion of the riser that is above grade and no longer protected, insulated, or supported by the ground. According to still other embodiments of the invention, a riser may be submerged in water, where the water similarly provides some UV ray protection, insulation and support for the submerged risers. Optionally, one or more exterior sleeves may be used in combination with submerging each riser to further protect, insulate, or support each riser.

As the name implies, the water wash system requires a supply of water by which the carbon dioxide is removed from the biogas stream. In some applications, such as a waste water treatment system, there may be a continuous supply of water. In the illustrated embodiment, a holding tank 40 is provided to supply the water. Water may be drawn from a pond or lake or otherwise be supplied from a well or from a municipal water supply. As previously discussed, the water may be chilled and/or compressed prior to being pumped to the absorption riser 110.

The water stream 50 and compressed gas streams each enter the top of each absorption risers 110 in a series arrangement as also shown in FIG. 1. A portion of the carbon dioxide is transferred from the compressed biogas stream 30 to the water stream 50 in each absorption riser 110. The compressed biogas stream 30 travels down a pipe to the lower portion of the absorption riser and the water stream 50 enters the top of the absorption riser. The compressed biogas rises and the water falls within each absorption riser 110, creating contact between the two streams. The partly purified biogas stream exits a first outlet 160 at the top of the initial absorption riser, and the mixed water stream 166 is internally pumped from the bottom of the absorption riser 110 to the top and exits a second outlet 165 also at the top of the absorption riser. Each subsequent absorption riser 110 in the series receives the partly purified biogas stream and mixed water stream from the prior absorption riser at the inlets and transfers additional carbon dioxide from the biogas stream to the water stream. The final absorption riser 110 contains the purified biogas stream which exits at the first outlet 160. According to the illustrated embodiment, the purified biogas stream 162 is provided to a storage tank 14 from which it may be used as a fuel. According to other embodiments and as illustrated in FIGS. 1-4, the purified biogas stream 162 may undergo some additional processing prior to use. For example, a first moisture removal vessel 26 and/or a subsequent desiccant dryer 27 may be provided to remove water from the purified biogas stream 162. Still other processing steps may be provided for polishing the gas to remove, for example, trace constituents or additional carbon dioxide still remaining in the biogas stream 162.

Figure 20:
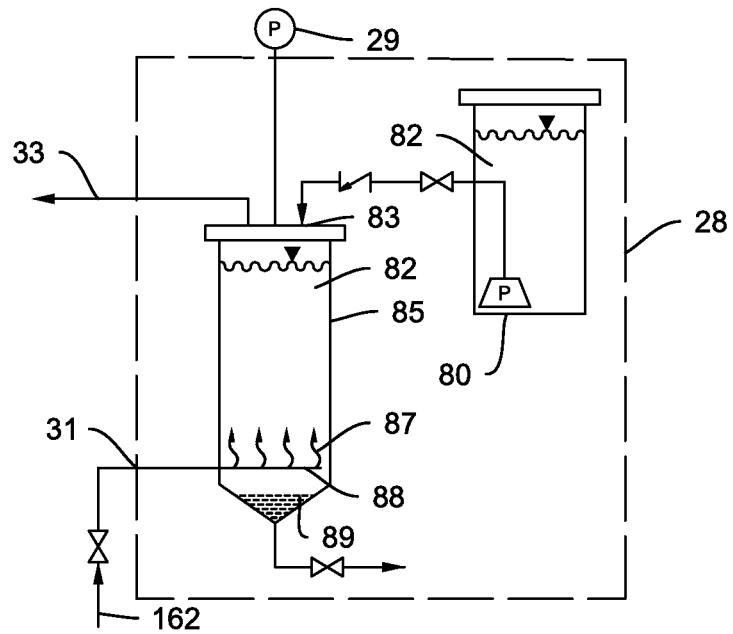
FIG. 20 is schematic representation of one embodiment of a polishing process incorporated into the biogas treatment system of FIG. 1.
Figure 21:
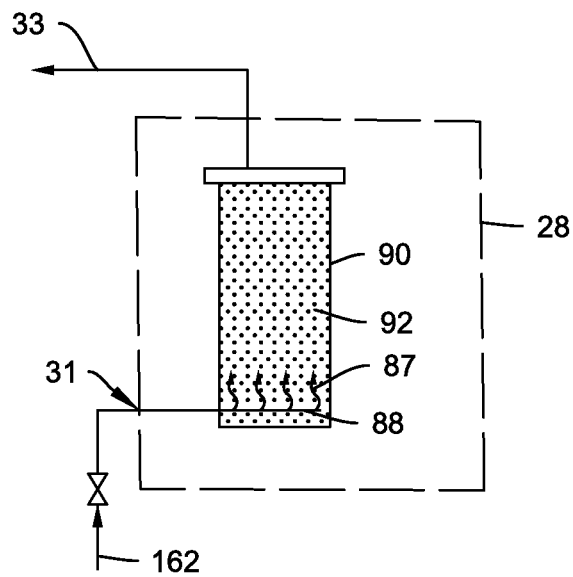
FIG. 21 is schematic representation of another embodiment of a polishing process incorporated into the biogas treatment system of FIG. 1.

With reference also to FIGS. 20 and 21, two exemplary polishing processes 28 are illustrated. In FIG. 20, the polishing process 28 uses a liquid polishing agent 82 which is a carbon dioxide (CO2) absorbent. According to one aspect of the invention, the polishing agent is an alkali material comprised of a hydroxide compound such as calcium hydroxide, sodium hydroxide, or potassium hydroxide. Optionally, the polishing agent may be an oxide compound such as calcium oxide. For purposes of discussion calcium hydroxide will be discussed in the form of a liquid polishing agent 82, however, this is not intended to be limiting. The calcium hydroxide is introduced into a first holding tank 80. The calcium hydroxide may be delivered directly to the first holding tank 80 in a liquid form as a mixture or solution. Optionally, the calcium hydroxide may be first introduced into the holding tank 80 in a solid form, for example, as powder and water, or other suitable liquid carrier, also introduced into the holding tank 80. A mixer may be used to combine the granules and the water into a solution suitable for delivery to the polishing tank 85. The liquid calcium hydroxide 82 is then delivered to an inlet 83 on the polishing tank 85.

Within the polishing tank 85, the polishing agent interacts with the purified biogas stream 162 to further remove any CO2 remaining in the biogas. The purified biogas stream 162 is delivered from the absorption riser 110 to the polishing tank 85 via a second inlet 31. Within the polishing tank 85 a perforated pipe 88 may be used to distribute biogas 87 throughout the polishing tank 85. Optionally, other distribution methods such as a nozzle or mixing element may be located within the polishing tank 85 to distribute the biogas 87. The biogas 87 interacts with the calcium hydroxide, Ca(OH)2, to remove CO2 remaining in the biogas 87. The calcium hydroxide, Ca(OH)2, interacts with the carbon dioxide (CO2) to generate calcium carbonate, CaCO3, and water, H20, forming a slurry 89 that settles to the bottom of the polishing tank 85. Further refined biogas 87 rises to the top of the polishing tank 85 and exits via an outlet 33 to storage or to a dryer 27, if present.

In FIG. 21, the polishing process 28 uses a solid polishing agent 92. Similar to the liquid polishing agent 82, the solid polishing agent is a hydroxide compound such as calcium hydroxide, sodium hydroxide, or potassium hydroxide. For purposes of discussion calcium hydroxide will again be discussed as the solid polishing agent 92, however, this is not intended to be limiting. A cannister 90 is provided in which the solid polishing agent 92 is located. It is contemplated that the cannister 90 and solid polishing agent 92 may be provided in combination as a replaceable unit, where the cannister 90 is changed out after a predefined volume of biogas 87 has passed through the cannister 90. Optionally, the cannister 90 may be a fixture in the treatment system and the solid polishing agent 92 may be removed and replaced within the cannister 90 after a predefined volume of biogas 87 has passed through the cannister 90. The purified biogas stream 162 is delivered from the absorption risers 110 to an inlet 31 on the cannister 90. Within the cannister 90 a perforated pipe 88 may be used to distribute biogas 87 throughout the cannister 90. Optionally, other distribution methods such as a nozzle or mixing element may be located within the canister 90 to distribute the biogas 87. The calcium hydroxide 92 is provided in a granular form, allowing the biogas 87 to flow through the solid polishing agent 92. In a manner similar to that discussed above with the liquid polishing agent 82, the biogas 87 interacts with the solid polishing agent 92, calcium hydroxide Ca(OH)2, to remove CO2 remaining in the biogas 87. The calcium hydroxide, Ca(OH)2, interacts with the carbon dioxide (CO2) in the biogas 87 to generate calcium carbonate, CaCO3, and water, H20, forming a slurry 89 that falls to the bottom of the cannister 90.

After a predefined volume of biogas 87 has passed through the cannister 90, the ability of the calcium hydroxide to further react with the CO2 in the biogas 87 will be depleted and the slurry in the cannister 90 will need to be cleaned out. As previously indicated, the cannister 90 and solid polishing agent 92 may be provided as a unit and the depleted cannister 90 with the slurry may be removed and a new cannister 90 and solid polishing agent 92 may be inserted. Optionally, the cannister 90 may have one or more openings by which the slurry may be removed and new solid polishing agent 92 introduced into the cannister 90 for further polishing of the purified biogas stream 162.

The mixed water stream 166 may be discharged and the carbon dioxide allowed to dissipate naturally. Optionally, the mixed water stream may be discharged into a tank for subsequent treatment. In still another embodiment, the carbon dioxide rich water may be utilized for another process within the waste water treatment system. In other applications, however, it may be desirable to recycle and reuse the water in which the carbon dioxide was dissolved. The water wash system may then include a flash riser 210, an air stripper riser 310, or a combination thereof. According to the illustrated embodiment, both a flash riser 210 and an air stripper riser 310 are included. The mixed water stream 166 from the final absorption riser 110 is provided as an input to the flash riser 210. As will be discussed in more detail below, the flash riser 210 separates methane dissolved in the mixed water stream 166. The first outlet 260 is connected back to the initial processing stage 12 such that the methane extracted from the mixed water stream 166 may be recovered in subsequent processing and a CO2 water stream is output from a second outlet 265 of the flash riser 210 to a second inlet 340 of the air stripping riser 310. A fan 75 discharges air into the first inlet 345 of the air stripping riser 310. As will be discussed in more detail below, the air stripping riser 310 separates the carbon dioxide from the water stream and the carbon dioxide is output from a first outlet 360. The reclaimed water may be used again within the water wash system and is pumped from the second outlet 365 of the air stripping riser 310 back to the holding tank 40.

Figure 7:
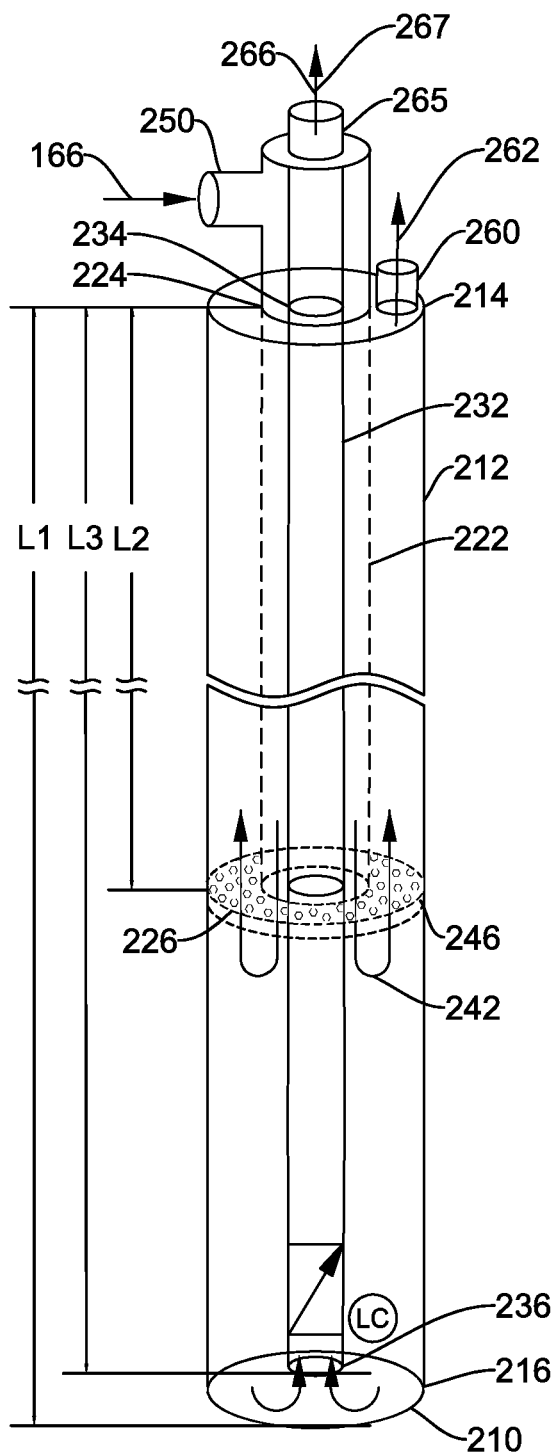
FIG. 7 is a front view of a flash riser from the biogas treatment system of FIG. 1.

Referring again to FIGS. 1 and 2, each of the illustrated systems includes both a flash riser 210 and an air stripper riser 310. With reference also to FIG. 7, an exemplary flash riser 210 is illustrated. During the absorption process, a small amount of methane may be absorbed into the water stream. This methane is referred to herein as the "slip gas." The flash riser 210 is configured to remove the slip gas from the mixed water stream 166 and return this methane to the supply for subsequent processing. The remaining water stream is passed on to the air stripping riser 310 where the carbon dioxide may be removed and the water reclaimed for subsequent use.

Each flash riser 210 includes multiple pipes. In the illustrated embodiment, the flash riser 210 includes an outer pipe 212, a first inner pipe 222, and a second inner pipe 232. According to the illustrated embodiment, each of the pipes is concentric to the others. Optionally, the first inner pipe 222 and the second inner pipe 232 may be positioned adjacent to each other or extend downward at different locations within the outer pipe 212. The outer pipe 212 has a first end 214, a second end 216, and a first length, L1. The first inner pipe 222 has a first end 224, a second end 226, and a second length, L2. The second inner pipe 232 has a first end 234, a second end 236, and a third length, L3. According to one embodiment of the invention, each of the flash risers 210 are installed in a vertical orientation, such that the first ends 214, 224, 234 of each pipe 212, 222, 232 are generally positioned at the top of each flash riser 210. The first inner pipe 222 extends for the second length, L2 into the outer pipe 212 and the mixed water stream 166 is delivered into the flash riser 210. According to the illustrated embodiment, the first inner pipe 222 is cylindrical and open at the second end 226. The mixed water stream 166 flows from the first inlet 250 and exits at the second end 226 of the first inner piper 222 The second inner pipe 232 extends for the third length, L3, through the first inner piper 222, beyond the second end 226 of the first inner pipe 222, and into the outer pipe 212. The second inner pipe 232 is cylindrical and the second end 236 of the second inner pipe 232 includes a check valve between the interior of the outer pipe 212 and the interior of the second inner pipe 232.

Each flash riser 210 includes an inlet and outlets to allow water and gas to flow into and out of the riser 210. A first inlet 250 receives the mixed water stream 166 and is located on the first end 214 of the outer pipe 212. The first inlet 250 is in fluid communication with the first end 224 of the first inner pipe 222 and establishes a flow path for the mixed water stream 166 into the flash riser 210. The first inner pipe 222 extends into the flash riser 210 for the length, L2, of the inner pipe 222. According to the illustrated embodiment, the second end 226 of the first inner pipe 222 terminates at a perforated coalescing disk 246 proximate the second end 216 of the first inner pipe 222. The mixed water stream 166 is dispensed into the flash riser 210 at the second end 226 of the first inner pipe 222. The pressure within the flash riser 210 is reduced such that the slip gas present in the mixed water stream 166 is desorbed and released within the outer pipe 212. The remaining water stream, however, continues to hold the carbon dioxide previously absorbed from the compressed biogas stream 30. The output water stream from the flash riser will be referred to herein as the CO2 water stream 266.

A first outlet 260 located at the first end 214 of the outer pipe 212 provides a flow path 261 for the slip gas 262 (i.e., the methane removed from the mixed water stream 166) to exit the flash riser 210. The first outlet 260 is in fluid communication with and receives the slip gas 262 from the interior of the outer pipe 212. A second outlet 265 is also located at the first end 214 of the outer pipe 212 and provides a flow path 267 for the CO2 water stream 266. The second outlet 265 is in fluid communication with the first end 234 of the second inner pipe 232. The CO2 water stream 266 enters the second end 236 of the second inner pipe 232 and travels up through the second inner pipe 232 to the second outlet 265. According to the illustrated embodiment, each of the outer pipe 212, first inner pipe 222, and second inner pipe 232 are concentric about a central axis. The second inner pipe 232 is located within the first inner pipe 222, which is, in turn, located within the outer pipe 212. As discussed above and for purposes of illustration in FIG. 7, the first end 214, 224, 234 of each pipe 212, 222, 232 ends at substantially the same point. It is contemplated that in various embodiments the first end 224, 234 of each of the first inner pipe 222 and the second inner pipe 232 may extend for a short distance beyond the first end 214 of the outer pipe 212 to facilitate connections between each pipe and an inlet or outlet. It is further contemplated that an inlet 250 or outlet 260, 265 may be positioned along and enter the outer pipe 212 via a side wall proximate the end of the flash riser 210. For example, the first inlet 250 is shown connecting generally orthogonally to a wall of the first inner pipe 222 beyond the first end 212 of the outer pipe and the second inner pipe 232 extends through an end wall of the first inner pipe 222 to connect to the second outlet 265. Alternately, the first inlet 250 or second outlet 265 may include a fixture connected to the first end 214 of the outer pipe 212 and comprise the necessary connections to establish the fluid flow paths from the inlet and outlet to the inner pipes extending into the outer pipe 212.

Each air stripping riser 310 also includes multiple pipes. In the illustrated embodiment, the air stripping riser 310 includes an outer pipe 312, a first inner pipe 322, and a second inner pipe 332. According to the illustrated embodiment, each of the pipes is concentric to the others. Optionally, the first inner pipe 322 and the second inner pipe 332 may be positioned adjacent to each other or extend downward at different locations within the outer pipe 312. The outer pipe 312 has a first end 314 and a second end 316. The first inner pipe 322 has a first end 324 and a second end 326. The second inner pipe 332 has a first end 334 and a second end 336. According to one embodiment of the invention, each of the air stripping riser 310 are installed in a vertical orientation, with the first end 314 of the outside pipe positioned at the top of the air stripping riser 310. The first ends 324, 334 of each inner pipe 322, 332 are generally positioned at a flange 311 located within the air stripping riser 310. When the air stripping riser 310 is used in conjunction with the absorption risers 110 and/or the flash riser 210, it is contemplated that the flange 311 on the air stripping riser 310 is located at the same height as the first end of the absorption riser 110 and/or flash riser 210. The first inner pipe 322 extends downward for a length into the outer pipe 312. The first inner pipe 322 receives an air flow 70 from a fan 75 at a first inlet 345 and delivers the air flow 70 proximate the bottom of the air stripping riser 310 but above a level at which water may be present in the bottom of the air stripping riser 310. According to the illustrated embodiment, the first inner pipe 322 is cylindrical and open at the second end 326. The air flow 70 is passed from the first inlet 345 and exits at the second end 326 of the first inner piper 322. The second inner pipe 332 extends through the first inner piper 322, beyond the second end 326 of the first inner pipe 322, and into the outer pipe 312. The second inner pipe 332 is cylindrical and the second end 336 of the second inner pipe 332 includes a check valve between the interior of the outer pipe 312 and the interior of the second inner pipe 332.

Each air stripping riser 310 includes a set of inlets and outlets to allow water and gas to flow into and out of the riser 310. A second inlet 340 of the air stripping riser 310 receives the CO2 water stream 266 from the flash riser 210. Optionally, if no flash riser 210 present, the second inlet 340 of the air stripping riser 310 may receive the mixed water stream 166 output from the absorption risers 110. The second inlet 340 is located proximate the top of the air stripping riser 310. According to the illustrated embodiment, a first intermediate pipe 341 and a second intermediate pipe 342 each extend from the second inlet 340 into the air stripping riser 310. The first intermediate pipe 341 extends upward and enters the air stripping riser 310 proximate the first end 314 of the outer pipe 312. The second intermediate pipe 342 enters the air stripping riser 310 proximate the flange 311 and the first ends 324, 334 of the first and second inner pipes 322, 332. The first intermediate pipe 341 is in fluid communication with a first nozzle 343 that sprays the CO2 water stream 266 into the top of the air stripping riser 310 and the second intermediate pipe 342 is in fluid communication with a second nozzle 344 that sprays the CO2 water stream 266 into the air stripping riser 310 at a midpoint along the air stripping riser 310. The dual entry points for the CO2 water stream 266 define separate segments of the air stripping riser 310 that may then interact with the air flow 70 entering the air stripping riser 310 to remove the carbon dioxide from the CO2 water stream 266.

As previously indicated, air flow 70 is provided at the first inlet 345 and into the first inner pipe 322, establishing a flow path for the air flow 70 into the air stripping riser 310. The first inner pipe 322 extends into the air stripping riser 310 for a length and, according to the illustrated embodiment, the second end 326 of the first inner pipe 322 terminates at a dispersion element 349 proximate the second end 316 of the first inner pipe 322. The air flow 70 is dispensed into the air stripping riser 310 at the second end 326 of the first inner pipe 322 as illustrated by the air flow path 367. The pressure within the air stripping riser 310 is further reduced from the flash riser 210 and is preferably maintained at or near atmospheric pressure. The reduction in pressure reduces the solubility of carbon dioxide in water facilitating the release of the carbon dioxide from the CO2 water stream 266 within the outer pipe 312. The air flow 70 is pumped into the bottom of the air stripping riser 310 such that the air flow 70 rises counter to the CO2 water stream 266 being sprayed into the top of the riser 310. The air flow 70 interacts with water droplets to facilitate release of the carbon dioxide and further carries the carbon dioxide toward the top of the air stripping riser 310.

A first outlet 360 located at the first end 314 of the outer pipe 312 provides a flow path 361 for the carbon dioxide 362 removed from the CO2 water stream 266 to exit the air stripping riser 310. The first outlet 360 is in fluid communication with and receives the carbon dioxide 362 from the interior of the outer pipe 312. A second outlet 365 is located proximate the first end 324 of the second inner pipe 232. As illustrated, the second inner pipe 332 is connected to a ninety degree bend pipe 337 and to a short outlet pipe 338 such that it extends out the side of the outer pipe 312. The second outlet 365 provides a flow path 367 for the reclaimed water stream 366. The second outlet 365 is in fluid communication with the first end 334 of the second inner pipe 332. The reclaimed water stream 366 enters the second end 336 of the second inner pipe 332 and travels up through the second inner pipe 332 to the second outlet 365. According to the illustrated embodiment, each of the outer pipe 312, first inner pipe 322, and second inner pipe 332 are concentric about a central axis. The second inner pipe 332 is located within the first inner pipe 322, which is, in turn, located within the outer pipe 312. The first end 324, 334 of each inner pipe 322, 332 ends proximate the flange 311 located within the outer pipe 312. The first inlet 345 and the second outlet 365 are connected to the first inner pipe 322 and the second inner pipe 332, respectively, and extend out through a wall of the outer pipe 312. Although the first end 314 of the outer pipe 312 extends for some distance beyond the flange 311, it is contemplated that in various embodiments the second inlet 340 may run directly into the outer pipe with a single intermediate pipe and the first end 314 of the outer pipe 312 may be positioned proximate the flange 311. Optionally, the first end 224, 234 of each of the first inner pipe 222 and the second inner pipe 232 may extend up to or for a short distance beyond the first end 314 of the outer pipe 312 without deviating from the scope of the invention.

Figure 8:
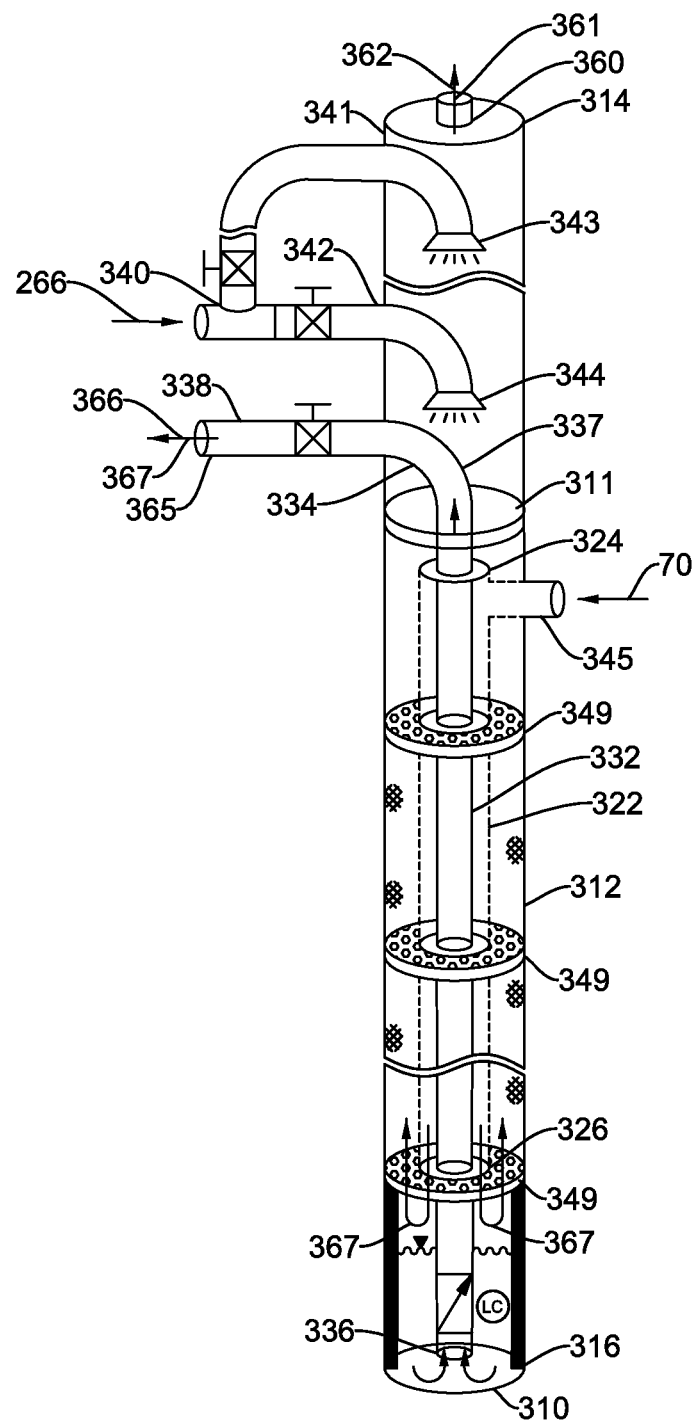
FIG. 8 is a front view of an air stripping riser from the biogas treatment system of FIG. 1.

It is further contemplated that each air stripping riser 310 may include packing material within at least a portion of the interior of the outer pipe 312 to further enhance the release of the carbon dioxide from the CO2 water stream 266. In FIG. 8, additional dispersion plates 349 are shown spaced apart within the outer pipe 312. One or more additional dispersion plates may be distributed along the length of the interior of the outer pipe 312 to continually redistribute the air flow 70 and CO2 water stream 266 as they travel through the interior of the pipe. It is also contemplated that packing material similar to that used in the absorption riser 110 may be inserted into the air stripping riser 310. With reference again to FIGS. 9 and 10, a flexible, porous material 170 may be rolled into a coil and inserted between the inner periphery of the outer pipe and the outer periphery of the first inner pipe. According to one embodiment of the invention, the flexible material 170 is a netting material, such as a geonet, including multiple holes throughout the material. As the CO2 water stream 266 passes through the air stripping riser 310, the netting and the multiple holes create numerous flow paths and opportunities for separating the CO2 water stream 266 into more droplets and, thereby, increasing the surface area of the water stream exposed to the air, facilitating release of the carbon dioxide into the air. In FIG. 10, a mesh material 180 may be formed into a basket or bag and is used to contain another bulk material 182 within the mesh. The mesh and bulk materials 180, 182 may be inserted into and removed from the interior of the outer pipe as a unit. Both the flexible material 170 and the mesh and bulk material combination 180, 182 facilitate cleaning of the packing material. The flexible material 170 may be removed and unrolled for cleaning. The mesh and bulk material 180, 182 may be pulled out of the outer pipe and the bulk material spread out for cleaning. Once clean, the flexible material 170 may be rolled back into a coil and inserted back into the outer pipe. Similarly, the bulk material 182 may be placed back into the mesh material 180 and inserted into the outer pipe.

According to still another embodiment of the invention the diameter and/or length of an absorption riser 110 may make the insertion of a material within the absorption riser challenging. Therefore, it is contemplated that the packing material may be a porous structure or material that is poured, blown, or pumped into the absorption riser 110. Initially, a mesh filter or grate may be inserted at a particular depth or length within the absorption riser to prevent the porous structure or material from passing beyond a certain point within the absorption riser 110. The filter or grate has openings of a smaller size than the size of individual members of the packing material, such that the packing material is stopped by the filter or grate while allowing the biogas and water streams flow through and around the packing material and filter or grate. It is further contemplated that the filter or grate may be connected to a cable or rod to facilitate cleaning or maintenance on the absorption riser. The cable or rod may have mixing devices attached or it may be used to pull the filter or grate out of the absorption riser 110 which, in turn, would pull out the packing material, allowing the packing material and/or the interior of the absorption riser to be inspected or maintained.

Figure 12:
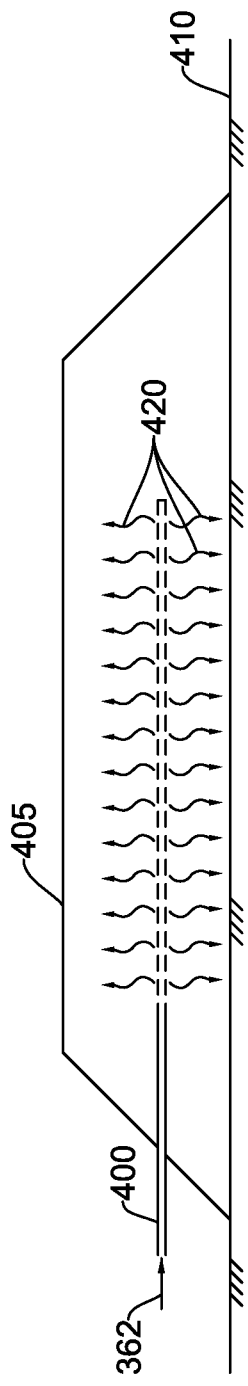
FIG. 12 is a side elevation view of one embodiment of a discharge pipe for releasing carbon dioxide removed from the biogas stream.
Figure 13:
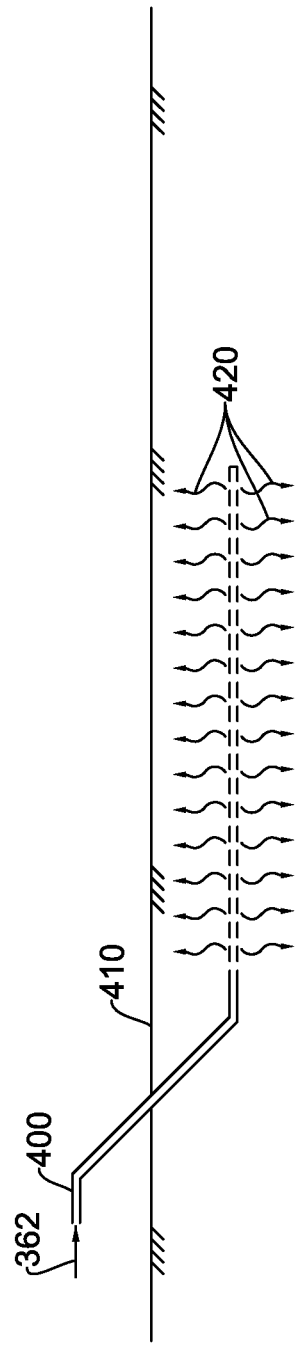
FIG. 13 is a side elevation view of another embodiment of a discharge pipe for releasing carbon dioxide removed from the biogas stream.
Figure 14:
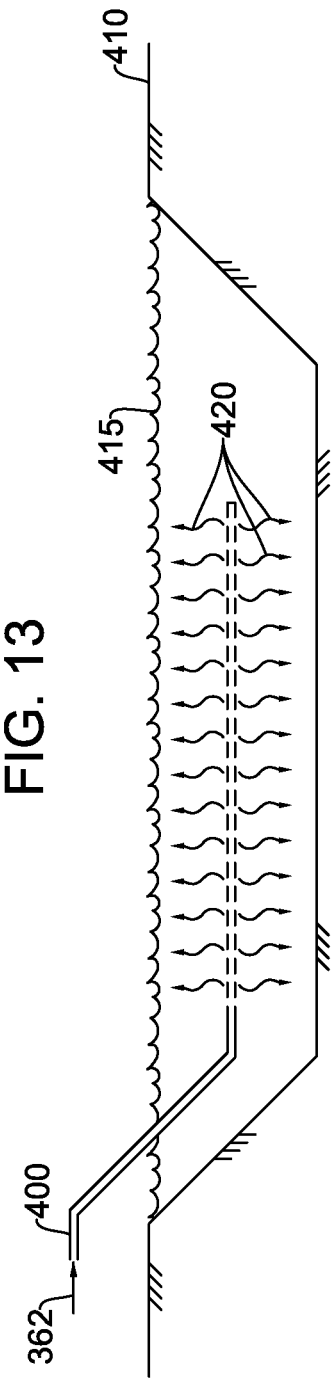
FIG. 14 is a side elevation view of another embodiment of a discharge pipe for releasing carbon dioxide removed from the biogas stream.

The carbon dioxide 362 extracted from the CO2 water stream 266 in the air stripping riser 310 may be vented directly from the first outlet 360 into the atmosphere. However, the potential exists that the carbon dioxide 362 stream may also include other contaminants. Therefore, it may be desirable to discharge the carbon dioxide 362 into the environment in another manner such that further processing may be performed on the carbon dioxide stream 362. Referring next to FIGS. 12-14, three exemplary off-gas discharge methods are illustrated. In FIG. 12, the carbon dioxide 362 is carried through a discharge pipe 400 into a bio-filter material 405. The bio-filter material is mounded above the ground 410 and the discharge pipe 400 is perforated along the length extending into the bio-filter material. The carbon dioxide 362 is vented into the bio-filter material as shown by the arrows 420. In FIG. 13, the carbon dioxide 362 is carried through a discharge pipe 400 for some distance above the ground 410 and is then buried below the ground 410. The discharge pipe 400 is perforated along the length extending below the ground, and the carbon dioxide 362 is vented into the ground as shown by the arrows 420. In FIG. 14, the carbon dioxide 362 is carried through a discharge pipe 400 into a water reservoir 415 formed in the ground 410. The water reservoir 415 may be naturally occurring such as a pond or lake or may be constructed by digging an area dug out of the ground 410. The discharge pipe 400 is perforated along the length extending under the water, and the carbon dioxide 362 is vented into the water reservoir as shown by the arrows 420. According to still another embodiment of the invention, it may be desirable to provide a thermal oxidization unit and the carbon dioxide 362 and other trace constituents may pass through the thermal oxidization unit prior to release into the atmosphere.

Figure 3:
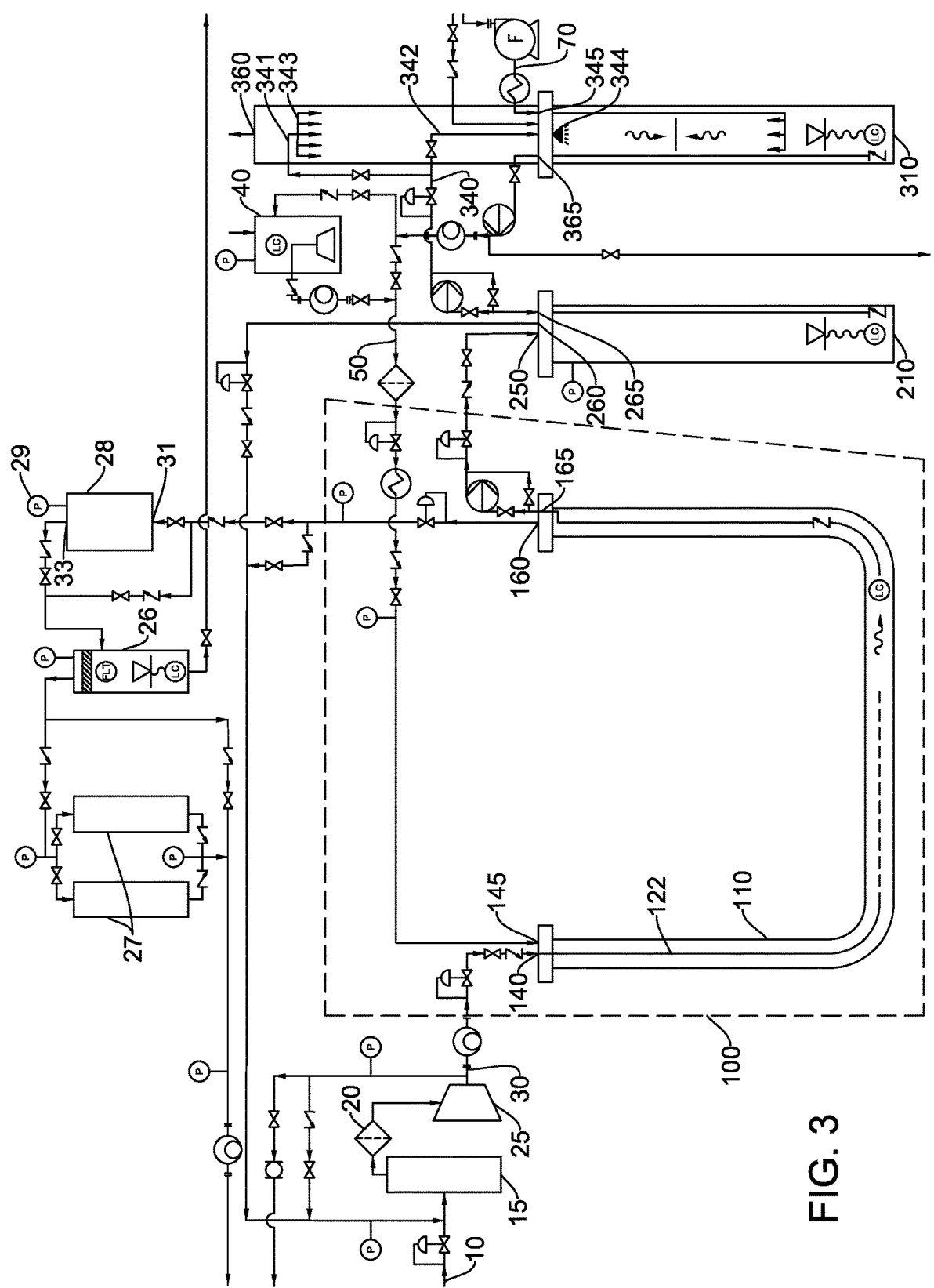
FIG. 3 is a schematic representation of an exemplary biogas treatment system incorporating another embodiment of the present invention.
Figure 4:
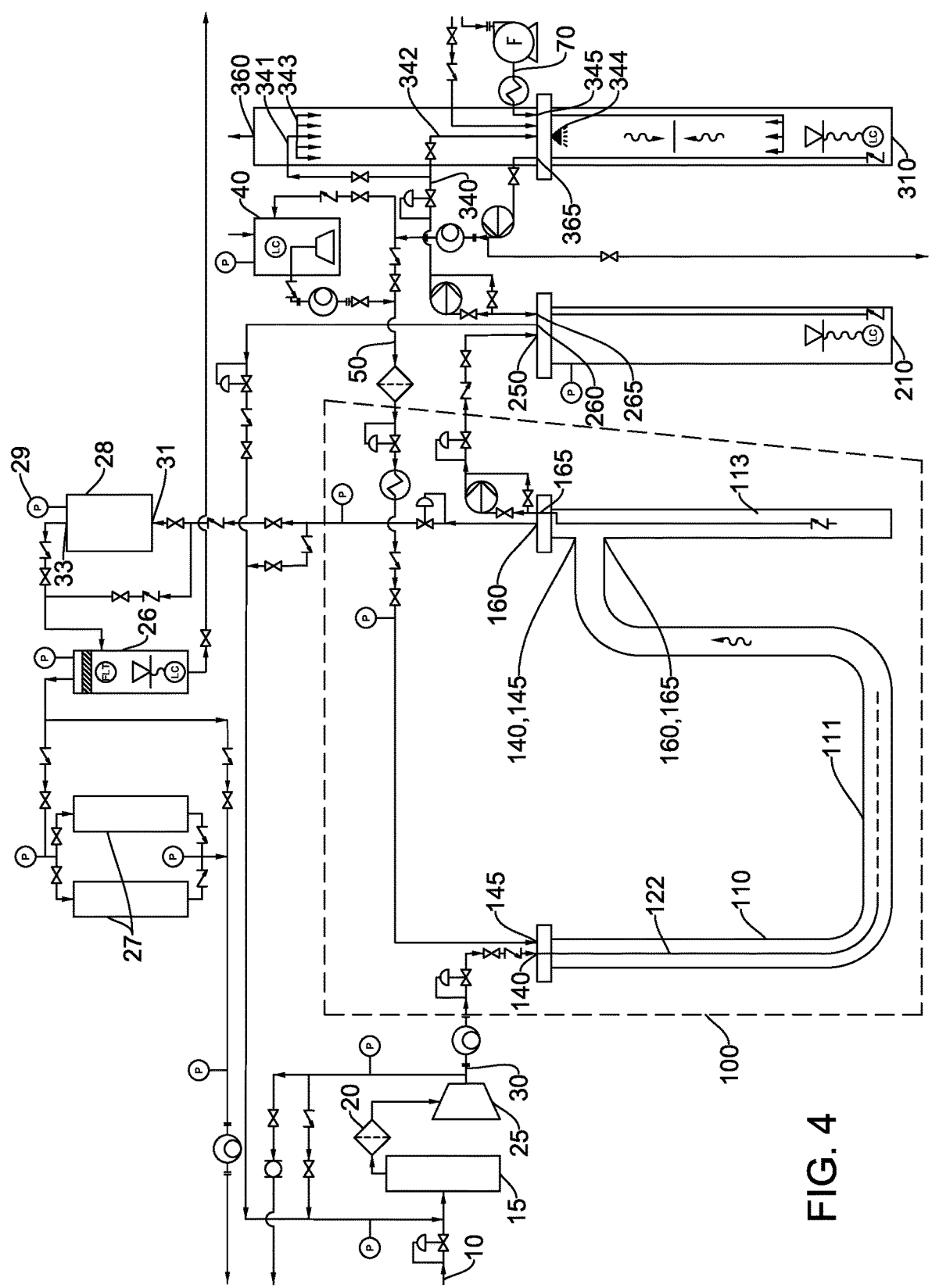
FIG. 4 is a schematic representation of an exemplary biogas treatment system incorporating another embodiment of the present invention.

Referring next to FIGS. 3 and 4, an exemplary biogas treatment system incorporating another embodiment of the present invention is illustrated. As discussed above with respect to FIG. 1, a biogas stream 10 is provided as an input to the system, where the biogas may be produced, for example, from an anaerobic decomposition process. Some initial processing of the biogas stream may occur prior to supplying the biogas stream to the water wash system. An optional hydrogen sulfide removal process 15 such as an iron sponge type system may be inserted in series with the biogas stream 10 to perform an initial removal of hydrogen sulfide present in the biogas stream. The biogas stream may also be passed through a filter 20 to remove particulate content. In addition, carbon dioxide has increased solubility characteristics with decreasing temperature and increasing pressure. The biogas stream is, therefore, passed through a compressor 25 to achieve an elevated pressure. The pressure range of the compressed biogas stream 30 may be between forty and two hundred pounds per square inch gauge (40-200 psig). According to one embodiment of the invention, the pressure range of the compressed gas is between about one hundred and one hundred fifty pounds per square inch gauge (100-150 psig). The compressed biogas may also be chilled, for example, to between thirty-five and sixty-eight degrees Fahrenheit (35-68° F.). The compressed and/or chilled biogas stream 30 is provided as an input to the water wash process.

Similar to the embodiment illustrated in FIGS. 1 and 2, the water wash process illustrated in FIG. 3 utilizes water to remove the carbon dioxide from the biogas stream. In the embodiments illustrated in FIGS. 1 and 2, however, the water and biogas streams flow in opposite directions (i.e., counter-current) to each other through the absorption risers 110. In the embodiments illustrated in FIGS. 3 and 4, the water and biogas streams flow in the same direction (i.e. concurrent) to each other through an absorption riser 110.

According to the illustrated embodiment, water is provided to a holding tank 40 from which a water stream 50 is provided to the water wash process. Water provided to the holding tank 40 may be chilled and/or under pressure to facilitate the water wash process. Optionally, the holding tank 40 may incorporate a chiller and/or a compressor to chill or pressurize the water prior to supplying it in the water stream. The water, for example, may be chilled to between thirty-five and sixty-eight degrees Fahrenheit (35-68° F.) and pressurized to mix with the compressed biogas stream 30 at about the same input pressure of the biogas stream.

In the biogas treatment system of FIG. 3, a single absorption riser 110 is provided. Referring also to FIG. 15, the absorption riser 110 includes multiple pipes. In the illustrated embodiment, the absorption riser 110 includes an outer pipe 112, a first inner pipe 122, and a second inner pipe 132. According to the illustrated embodiment, each of the inner pipes 122, 132 is concentric to the outer pipe 112. Optionally, the inner pipes 122, 132 may be positioned at different locations (e.g., along the interior wall) within the outer pipe 112. The outer pipe 112 has a first end 114 and a second end 116. The first inner pipe 122 has a first end 124 and a second end 126. The second inner pipe 132 has a first end 134 and a second end 136. The outer pipe 112 also includes a first segment 117, a second segment 118, and a third segment 119. It is contemplated that the absorption riser 110 may be buried within the ground or submerged below water. Optionally, the outer pipe 112 and the inner pipes may be formed of a flexible material and may extend in one or more rows or be coiled up and placed, for example, on the ground in a substantially horizontal configuration.

If the pipes are buried or submerged, the first segment 117 extends downward where the first end 114 of the outer pipe 112 may be located at a surface level. The first inner pipe 122 is located within the first segment 117, where the first end 124 of the first inner pipe 122 is generally positioned at the first end 114 of the outer pipe 112. The second segment 118 extends generally in a horizontal direction, and the first inner pipe 122 also includes a horizontal segment 128 that extends, at least for a portion of the horizontal direction, within the outer pipe 112. The horizontal segment 128 includes a plurality of perforations 127 located along the length of the horizontal segment 128 from which the compressed biogas stream 30 may be released into the water flowing through the outer pipe. It is contemplated that the perforations 127 may also be located along the descending portion of the inner pipe 122 within the first segment 117 of the outer pipe 112. The third segment 119 extends upward back to the surface level. The second inner pipe 132 is located within the third segment 119 of the outer pipe 112. The second inner pipe 132 is cylindrical and the second end 136 of the second inner pipe 132 is located proximate the transition between the second segment 118 and the third segment 19 of the outer pipe 112. The first end 134 of the second inner pipe 132 is located proximate the second end of the outer pipe. The second end 136 of the second inner pipe 132 includes a check valve between the interior of the outer pipe 112 and the interior of the second inner pipe 132, where the check valve is controlled to allow the mixed water stream to enter the second inner pipe 132 and be drawn up and out of the absorption riser 110 through the second inner pipe.

If the pipes are laid out in rows or coiled up and placed on the ground, the first segment 117 extends for a portion of the absorption riser 110 and the first end 114 of the outer pipe 112 is located at a first end of the absorption riser 110. The first inner pipe 122 is located within the first segment 117, where the first end 124 of the first inner pipe 122 is generally positioned at the first end 114 of the outer pipe 112. The second segment 118 extends for a second portion of the absorption riser 110, and the first inner pipe 122 also extends at least for a portion of the second segment 118. The first inner pipe 122 includes a plurality of perforations 127 located along the length of the first inner pipe within the second segment 118 from which the compressed biogas stream 30 may be released into the water flowing through the outer pipe 112. The third segment 119 extends for a third portion of the outer pipe 112, and the second inner pipe 132 is located within the third segment 119 of the outer pipe 112. The second inner pipe 132 is cylindrical and the second end 136 of the second inner pipe 132 is located proximate the transition between the second segment 118 and the third segment 119 of the outer pipe 112. The first end 134 of the second inner pipe 132 is located proximate the second end of the outer pipe. The second end 136 of the second inner pipe 132 includes a check valve between the interior of the outer pipe 112 and the interior of the second inner pipe 132, where the check valve allows the mixed water stream to flow in one direction to enter the second inner pipe 132 and be drawn up and out of the absorption riser 110 through the second inner pipe.

In the biogas treatment system of FIG. 4, the single absorption riser 110 of FIG. 3 may be divided into two portions, where a first portion 111 includes the first segment 117 and the second segment 118 of the absorption riser 110 as discussed above with respect to FIG. 3. The second portion 113 includes the third segment 119 of the absorption riser 110 as discussed above with respect to FIG. 3. Referring also to FIG. 17, the absorption riser 110 includes multiple pipes. In the illustrated embodiment, the absorption riser 110 includes an outer pipe 112, a first inner pipe 122, and a second inner pipe 132. According to the illustrated embodiment, each of the inner pipes 122, 132 is concentric to the outer pipe 112. Optionally, the inner pipes 122, 132 may be positioned at different locations (e.g., along the interior wall) within the outer pipe 112. The outer pipe 112 is divided into two lengths, where the first length 112A of the outer pipe has a first end 114A and a second end 116B. The outer pipe 112 also includes a first segment 117 and a second segment 118 extending within the first length 112A of the outer pipe 112. A third segment 119 extends for the second length 112B of the outer pipe 112. The first inner pipe 122 has a first end 124 and a second end 126, where the first end 124 is proximate the first end 114A of the first length 112A of the outer pipe. It is contemplated that the absorption riser 110 may be buried within the ground or submerged below water. Optionally, the outer pipe 112 and the inner pipes may be formed of a flexible material and may extend in one or more rows or be coiled up and placed, for example, on the ground in a substantially horizontal configuration.

If the pipes are buried or submerged, the first segment 117 extends downward where the first end 114A of the first length 112A of the outer pipe 112 may be located at a surface level. The first inner pipe 122 is located within the first segment 117, where the first end 124 of the first inner pipe 122 is generally positioned at the first end 114A of the first length 112A of the outer pipe 112. The second segment 118 extends generally in a horizontal direction, and the first inner pipe 122 also includes a horizontal segment 128 that extends, at least for a portion of the horizontal direction, within the outer pipe 112. The horizontal segment 128 includes a plurality of perforations 127 located along the length of the horizontal segment 128 from which the compressed biogas stream 30 may be released into the water flowing through the outer pipe. It is contemplated that the perforations 127 may also be located along the descending portion of the inner pipe 122 within the first segment 117 of the outer pipe 112. Optionally, a series of nozzles or other gas injectors may be located along the length of the inner pipe 122, where each nozzle disperses a portion of the biogas stream within the outer pipe 112. According to still another option, multiple inner pipes 122 may be provided, where each inner pipe 122 includes a series of perforations 127 or nozzles spaced along the length of each inner pipe 122 to facilitate dispersion of the biogas stream 30 throughout the interior of the outer pipe 112. The second segment 118 may further include a rising section, where at least the first length 112A of the outer pipe and, optionally, the inner pipe 122 extend for a distance back toward the surface level.

If the pipes are laid out in rows or coiled up and placed on the ground, the first segment 117 extends for a portion of the absorption riser 110 and the first end 114A of the outer pipe 112 is located at a first end of the absorption riser 110. The first inner pipe 122 is located within the first segment 117, where the first end 124 of the first inner pipe 122 is generally positioned at the first end 114 of the outer pipe 112. The second segment 118 extends for a second portion of the absorption riser 110, and the first inner pipe 122 also extends at least for a portion of the second segment 118. The first inner pipe 122 includes a plurality of perforations 127 located along the length of the first inner pipe within the second segment 118 from which the compressed biogas stream 30 may be released into the water flowing through the outer pipe 112. It is contemplated that the perforations 127 may also be located along the portion of the inner pipe 122 within the first segment 117 of the outer pipe 112. The third segment 119 extends for a third portion of the outer pipe 112, and the second inner pipe 132 is located within the third segment 119 of the outer pipe 112. According to one embodiment, the first and second segments 117, 118 defining the first length 112A of the outer pipe 112 may be located generally horizontally, for example, on the ground and the second length 112B of the outer pipe 112 may extend vertically, for example, buried or submerged below a surface level of ground or water.

The second length 112B of the outer pipe 112 defines a substantially vertical pipe having a first end 114B and a second end 116B. The second end 116A of the first length 112A of the outer pipe is connected proximate the first end 114B of the second length 112B of the outer pipe. The second inner pipe 132 is located within the third segment 119 of the outer pipe 112, which corresponds to the second length 112B of the outer pipe. The second inner pipe 132 has a first end 134 and a second end 136. The second inner pipe 132 is cylindrical and the second end 136 of the second inner pipe 132 is located proximate the second end 116B of the second length 112B of the outer pipe. The first end 134 of the second inner pipe 132 is located proximate the first end 114B of the second length 112B of the outer pipe. The second end 136 of the second inner pipe 132 includes a check valve between the interior of the second length 112B of the outer pipe 112 and the interior of the second inner pipe 132, where the check valve allows the mixed water stream to flow in one direction to enter the second inner pipe 132 and be drawn up and out of the absorption riser 110 through the second inner pipe.

With reference again to FIGS. 3-4 and 15-17, the absorption riser 110 includes a set of inlets and outlets to allow water and biogas to flow into and out of the riser 110. A first inlet 140 receives the compressed biogas stream 30 and is located on the first end 114 of the outer pipe 112. The first inlet 140 is in fluid communication with the first end 124 of the first inner pipe 122 and establishes a flow path for the compressed biogas stream 30 into the absorption riser 110. As previously indicated, the first inner pipe 122 extends into through the first segment 117 and into the second segment 118 of the outer pipe 112, and the second end 126 of the first inner pipe 122. A second inlet 145 receives the water stream 50 and is located on the first end 114 of the outer pipe 112. The second inlet 145 is in fluid communication with the first end 114 of the outer pipe 112 to dispense the water stream 50 from the first end of the absorption riser 110. The water stream 50 flows through to the second end of the absorption riser. The compressed biogas stream 30 is dispensed into the water flow from the perforations 127 in the first inner pipe 122 and flows toward the second end of the absorption riser.

As the compressed biogas stream 30 and the water stream 50 flow along the horizontal portion of the absorption riser 110 the two streams mix and the carbon dioxide within the compressed biogas stream 30 is dissolved into the water. Although small amounts of methane may be absorbed in the water, the majority of the methane remains unabsorbed. The methane is lighter than the mixed water stream containing carbon dioxide. With reference to FIGS. 3 and 15, the methane rises to the second end 116 of the absorption riser 110. The mixed water stream 166 including the carbon dioxide absorbed from the biogas stream is heavier than the methane and remains at the end of the horizontal segment of the absorption riser at the transition to the upward segment. A first outlet 160 located at the second end 116 of the outer pipe 112 provides a flow path 161 for the purified biogas stream 162 to exit the absorption riser 110. The first outlet 160 is in fluid communication with and receives the purified biogas stream 162 from the interior of the outer pipe 112. With reference to FIGS. 4 and 17, the flow in the first length 112A of the outer pipe created by the water stream 50 and the biogas stream 30 establish a flow through the first length 112A of the outer pipe 112 and into the second length 112B of the outer pipe. The mixed water stream then falls to the second end 116B of the second length 112B of the outer pipe and the methane rises to the first end 114B of the second length 112B of the outer pipe. A first outlet 160 located at the first end 114B of the second length 112B of the outer pipe 112 provides a flow path 161 for the purified biogas stream 162 to exit the absorption riser 110. The first outlet 160 is in fluid communication with and receives the purified biogas stream 162 from the interior of the outer pipe 112. A second outlet 165 is also located proximate the first outlet 160 and provides a flow path 167 for the mixed water stream 166. The second outlet 165 is in fluid communication with the first end 134 of the second inner pipe 132. The mixed water stream 166 enters the second end 136 of the second inner pipe 132 and travels up through the second inner pipe 132 to the second outlet 165. As discussed above and for purposes of illustration in FIG. 4, the first ends 114, 124, of the outer pipe 112 and the first inner pipe 122 end at substantially the same point. Similarly, the first end 134 of the second inner pipe 132 and the second end 116 of the outer pipe 112 end at substantially the same point. It is contemplated that in various embodiments the first end 124, 134 of each of the first inner pipe 122 and the second inner pipe 132 may extend for a short distance beyond either end of the outer pipe 112 to facilitate connections between each pipe and an inlet or outlet.

Because the interaction of the water stream and the biogas stream is reduced when the streams are travelling in the same direction rather than travelling in opposite directions, transfer of carbon dioxide from the compressed biogas stream 30 to the water stream 50 occurs at a reduced rate per length of travel. Thus, the embodiment illustrated in FIG. 3 is better suited for applications in which a lengthy horizontal segment of the absorption riser is available. It is contemplated that each pipe of the absorption riser may be formed of a flexible material and coiled or laid out in rows alternating back and forth adjacent to each other. According to one embodiment, the absorption riser may extend along the ground in a generally horizontal orientation. According to another embodiment, the absorption riser 110 may be routed into a pond, lake, or other available water source. The water may provide some protection and/or insulation for the absorption riser 110. The absorption riser may extend in numerous configurations, such as a straight line, a curved path, an alternating back-and-forth route, or a combination thereof to increase the length of the horizontal segment. It is contemplated that the horizontal segment of the absorption riser 110 may extend for one hundred feet or longer before the absorption riser 110 transitions to the upward segment. Optionally, a portion, or all, of the absorption riser may include an external sleeve to provide further protection and/or insulation. The sleeve may further provide weight to the absorption riser 110 if it is installed in an underwater application to reduce buoyancy and to help keep the absorption riser 110 along the bottom of the pond, lake, or other water source.

To increase the interaction between the water stream 50 and the biogas stream 30, it is contemplated that one or more mixing elements may be included along the length of travel. The mixing elements may be powered, for example, a rotating member within the pipe, or preferably, may be passive mixing elements. The passive mixing elements are configured to disrupt a linear flow path through the pipes, causing the water stream 50 and the biogas stream 30 to intermix their flows along the length of the absorption riser. With reference to FIGS. 15 and 17, it is contemplated that a dispersion plate 149 may be included within the outer pipe 112. The dispersion plate may be located proximate the inlets to disperse a flow across the interior of the absorption riser 110. Optionally, one or more dispersion plates 149 may be located beyond the second end 126 of the first inner pipe 122 to encourage mingling of the two flows. With reference also to FIGS. 18 and 19, the interior of the absorption riser 110 may have different configurations. In FIG. 18, the horizontal segment 128 of the inner pipe is illustrated with perforations 127 distributed around the pipe. The compressed biogas stream 30 escapes through the perforations 127 into the water stream 50 flowing in the same direction through the pipe. Optionally, and as shown in FIGS. 17 and 19, the horizontal segment 118 of the outer pipe 112 may include packing material 190 within at least a portion of the interior of the horizontal segment 118 to further enhance the release of the carbon dioxide from the water stream 50. The compressed biogas stream 30 may be discharged into the horizontal segment 118 in advance of the packing material 190 so that the compressed biogas stream 30 and the water stream 50 travel through the packing material 190 and, thereby increase contact between the two streams. A partially mixed stream 55 is illustrated as continuing on along the horizontal segment of the absorption riser 110. It is further contemplated that a combination of the two embodiments may be utilized in which the horizontal segment 128 of the inner pipe extends into a segment of the outer pipe 112 that has packing material 190 located therein.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

I claim:

1. A system for separating gaseous mixtures from a biogas stream, the system comprising:
   an outer pipe having a first end, a second end, and a length;
   an inner pipe within the outer pipe, the inner pipe having a first end, a second end, and a length, wherein:
   the length of the inner pipe is less than the length of the outer pipe,
   the first end of the inner pipe is proximate the first end of the outer pipe,
   the inner pipe extends from the first end of the outer pipe into the outer pipe, and
   the inner pipe includes a plurality of perforations distributed along a portion of the length of the inner pipe;
   a first inlet in fluid communication with the first end of the inner pipe to deliver the biogas stream into the inner pipe, wherein the biogas stream is dispensed from the inner pipe into the outer pipe via the plurality of perforations;
   a second inlet in fluid communication with the first end of the outer pipe to deliver a water stream into the outer pipe, wherein the water stream contacts the biogas stream within the outer pipe to separate carbon dioxide from the biogas stream, resulting in a purified biogas stream and a mixed water stream within the outer pipe, wherein methane in the purified biogas stream causes the purified biogas stream to rise to a top of the outer pipe;
   a first outlet in fluid communication with the second end of the outer pipe to deliver the purified biogas stream from the outer pipe;
   a second outlet in fluid communication with the second end of the outer pipe to deliver the mixed water stream from the outer pipe; and
   a riser connected to the outer pipe, wherein the riser includes:
   an inlet to receive the mixed water stream and the purified gas stream from the first outer pipe, wherein methane in the purified biogas stream causes the purified biogas stream to rise to a top of the riser;
   an outlet for the purified gas stream; and
   an outlet for the mixed water stream.

2. The system of claim 1 further comprising at least one dispersion element mourned within the outer pipe to distribute the flow of at least one of the biogas stream and the water stream within an interior of the outer pipe.

3. The system of claim 1 further comprising a removable packing material inserted within the outer pipe and located in both a first flow path of the water stream and a second flow path of the biogas stream, wherein the packing material causes each of the first and the second flow paths to mix.

4. The system of claim 3 wherein the packing material is a netting material rolled into a coil and inserted within the outer pipe.

5. The system of claim 3 wherein the packing material includes a mesh material and a bulk material contained within the mesh material.

6. The system of claim 1 wherein:
the outer pipe includes a first segment, a second segment, and a third segment,
the first segment extends from the first end of the outer pipe along a first portion of the length of the outer pipe,
the first end of the outer pipe is located at or above grade and the first segment extends from above grade to below grade,
the second segment extends from the first segment along a second portion of the length of the outer pipe and is located below grade,
the third segment extends from the second segment to the second end of the outer pipe,
the second end of the outer pipe is located at or above grade and the third segment extends from below grade to above grade,
the system further comprises a second inner pipe extending from the second end and into the third segment of the outer pipe, wherein:
the mixed water stream enters the second inner pipe, and
the second outlet is in fluid communication with the second inner pipe to deliver the mixed water stream.

7. The system of claim 1 wherein the outer pipe is arranged in a generally horizontal plane at or above grade.

8. The system of claim 1, wherein:
the riser includes a second outer pipe and a second inner pipe,
the second outer pipe has a first end, a second end, and a length,
the second inner pipe has a first end, a second end, and extends within the second outer pipe from the first end of the second outer pipe toward the second end of the second outer pipe, wherein:
the second end of the outer pipe connects to the second outer pipe proximate the first end of the second outer pipe,
the first outlet and the second outlet are the second end of the outer pipe,
the outlet for the purified gas stream on the riser is a third outlet at the first end of the second outer pipe,
the second inner pipe receives the mixed water stream at the second end of the second inner pipe, and
the outlet for the mixed water stream on the riser is a fourth outlet at the first end of the second inner pipe.

9. The system of claim 1 further comprising:
a polishing tank in fluid communication with the outlet of the riser to receive the purified biogas stream; and
a polishing agent within the polishing tank, wherein the polishing agent is selected to remove residual carbon dioxide from the purified biogas stream.

10. The system of claim 9 wherein the polishing agent is an alkali material.

11. A method for separating gaseous mixtures from a biogas stream, the method comprising the steps of:
supplying the biogas stream to a first inlet in fluid communication with an inner pipe;
supplying a water stream to a second inlet in fluid communication with an outer pipe, wherein:
the outer pipe has a first end, a second end, and a length,
the inner pipe has a first end, a second end, and a length less than the length of the outer pipe,
the first end of the inner pipe is proximate the first end of the outer pipe,
the first inlet is in fluid communication with the first end of the inner pipe, and
the second inlet is in fluid communication with the first end of the outer pipe;
delivering the biogas stream from the inner pipe to the outer pipe via a plurality of perforations distributed along a portion of the length of the inner pipe;
mixing the biogas stream with the water stream within the outer pipe to remove carbon dioxide from the biogas stream, resulting in a purified biogas stream rising to a top of the outer pipe and a mixed water stream flowing to a bottom of the outer pipe;
dispensing the purified biogas stream from a first outlet located at the second end of the outer pipe; and
dispensing the mixed water stream from a second outlet located at the second end of the outer pipe.

12. The method of claim 11 wherein the step of mixing the biogas stream with the water stream further comprises the step of passing at least one of the biogas stream and the water stream across at least one dispersion element mounted within the outer pipe to distribute the flow of at least one of the biogas stream and the water stream within an interior of the outer pipe.

13. The method of claim 11 wherein the step of mixing the biogas stream with the water stream further comprises the step of passing the biogas stream and the water stream through a removable packing material inserted within the outer pipe.

14. The method of claim 13 wherein the packing material is a netting material rolled into a coil and inserted within the outer pipe.

15. The method of claim 13 wherein the packing material includes a mesh material and a bulk material contained within the mesh material.

16. The method of claim 11 further comprising the step of:
transferring the purified biogas stream from the first outlet to an inlet of a polishing tank; and
removing residual carbon dioxide from the purified biogas stream via a polishing agent located in the polishing tank.

17. The method of claim 16 wherein the polishing agent is an alkali material.

* * * * *